US011938322B2

United States Patent
de Zambotti et al.

(10) Patent No.: US 11,938,322 B2
(45) Date of Patent: Mar. 26, 2024

(54) SLOW WAVE ACTIVITY OPTIMIZATION BASED ON DOMINANT PERIPHERAL NERVOUS SYSTEM OSCILLATIONS

(71) Applicant: SRI International, Menlo Park, CA (US)

(72) Inventors: Massimiliano de Zambotti, Burlingame, CA (US); Fiona C. Baker, San Jose, CA (US); Ian M. Colrain, Redwood City, CA (US); Mohamad Forouzanfar, Menlo Park, CA (US); Aimee Goldstone, Menlo Park, CA (US); Adrian Willoughby, Johor (MY)

(73) Assignee: SRI International, Menlo Park, CA (US)

( * ) Notice: Subject to any disclaimer, the term of this patent is extended or adjusted under 35 U.S.C. 154(b) by 72 days.

(21) Appl. No.: 16/631,143

(22) PCT Filed: Jul. 17, 2018

(86) PCT No.: PCT/US2018/042493
§ 371 (c)(1),
(2) Date: Jan. 14, 2020

(87) PCT Pub. No.: WO2019/018400
PCT Pub. Date: Jan. 24, 2019

(65) Prior Publication Data
US 2020/0222699 A1 Jul. 16, 2020

Related U.S. Application Data

(60) Provisional application No. 62/533,299, filed on Jul. 17, 2017.

(51) Int. Cl.
*A61N 1/36* (2006.01)
*A61B 5/00* (2006.01)
(Continued)

(52) U.S. Cl.
CPC ...... *A61N 1/36128* (2013.01); *A61B 5/02108* (2013.01); *A61B 5/316* (2021.01);
(Continued)

(58) Field of Classification Search
CPC ............ A61N 1/36128; A61B 5/02108; A61B 5/4812
See application file for complete search history.

(56) References Cited

U.S. PATENT DOCUMENTS

2008/0081941 A1 4/2008 Tononi
2009/0292180 A1* 11/2009 Mirow ................... G16H 10/20
600/300
(Continued)

FOREIGN PATENT DOCUMENTS

EP 3181041 A1 6/2017
JP 2016-520348 A 7/2016
(Continued)

OTHER PUBLICATIONS

Cheryl C.H. Yang et al., Relationship between electroencephalogram slow-wave magnitude and heart rate variability during sleep in humans, Neuroscience Letters, vol. 329, Issue 2, 2002, pp. 213-216, ISSN 0304-3940, https://doi.org/10.1016/S0304-3940(02)00661-4. viewed on Aug. 13, 2021.*
(Continued)

*Primary Examiner* — Nathan J Jenness
*Assistant Examiner* — James Moss
(74) *Attorney, Agent, or Firm* — Dicke, Billig & Czaja, PLLC

(57) ABSTRACT

Embodiments in accordance with the present disclosure are directed to methods and apparatuses used for slow wave activity (SWA) optimization. An example method includes receiving one or more bio-signals from a user and classifying sleep stages by processing the bio-signals. The method
(Continued)

further include determining dominant peripheral nervous system (PNS) oscillations based on the bio-signals and as a function of time and stage of sleep, and characterizing at least one property of the dominant PNS oscillations, including a phase, a phase shift, an amplitude, and/or frequency. The method further include providing an indication of an optimal window for maximizing SWA generation based on the phase, the phase shift, the amplitude, or the frequency. The indication is provided to stimulation circuitry that delivers stimulation to the user within the optimal window. Feedback is provided responsive to the stimulation based on an EEG signal of the user.

20 Claims, 14 Drawing Sheets

(51) Int. Cl.
  *A61B 5/021* (2006.01)
  *A61B 5/316* (2021.01)
  *A61B 5/318* (2021.01)
  *A61B 5/369* (2021.01)
  *A61B 5/398* (2021.01)

(52) U.S. Cl.
  CPC .............. *A61B 5/318* (2021.01); *A61B 5/369* (2021.01); *A61B 5/398* (2021.01); *A61B 5/4812* (2013.01)

(56) References Cited

U.S. PATENT DOCUMENTS

| | | | |
|---|---|---|---|
| 2014/0057232 A1* | 2/2014 | Wetmore | A61N 1/36025 434/236 |
| 2015/0324701 A1 | 11/2015 | Park et al. | |
| 2015/0374951 A1 | 12/2015 | Garcia Molina et al. | |
| 2016/0045706 A1* | 2/2016 | Garcia Molina | A61M 21/02 600/27 |
| 2016/0058970 A1 | 3/2016 | Garcia Molina et al. | |
| 2016/0082222 A1 | 3/2016 | Garcia Molina et al. | |
| 2016/0228705 A1 | 8/2016 | Crowder et al. | |
| 2017/0196474 A1 | 7/2017 | Garcia Molina et al. | |
| 2017/0304587 A1 | 10/2017 | Santostasi et al. | |
| 2017/0340855 A1* | 11/2017 | Soulet De Brugiere | A61B 5/6814 |

FOREIGN PATENT DOCUMENTS

| | | |
|---|---|---|
| WO | 2014/167457 A1 | 10/2014 |
| WO | 2016179407 A1 | 11/2016 |
| WO | 2017109621 A1 | 6/2017 |
| WO | 2018051354 A1 | 3/2018 |

OTHER PUBLICATIONS

Gabrielle Brandenberger et al., Is slow wave sleep an appropriate recording condition for heart rate variability analysis?, Autonomic Neuroscience, vol. 121, Issues 1-2, 2005, pp. 81-86, ISSN 1566-0702, https://doi.org/10.1016/j.autneu.2005.06.002. viewed on Aug. 14, 2021.*
1. Massimiliano de Zambotti, PhD, Adrian R. Willoughby, PhD, Peter L. Franzen, PhD, Duncan B. Clark, MD, Phd, Fiona C. Baker, PhD, Ian M. Colrain, PhD, K-Complexes: Interaction between the Central and Autonomic Nervous Systems during Sleep, Sleep, vol. 39, Issue 5, May 2016, pp. 1129-1137.
2. CL Tegeler, LJ Howard, KD Schmidt, JF Cook, S Kumar, SL Simpson, SW Lee, L Gerdes, CH Tegeler, 0389 Use of a Closed-Loop Acoustic Stimulation Neurotechnology Improves Symptoms of Moderate To Severe Insomnia: Results of a Placebo-Controlled Trial, Sleep, vol. 40, Issue suppl_1, Apr. 28, 2017, p. A145.
3. Mohsen Naji, Giri P. Krishnan, Elizabeth A McDevitt, Maxim Bazhenov, Sara C. Mednick, Coupling of autonomic and central events during sleep boosts declarative memory consolidation, Neurology of Learning and Memory, vol. 157, Jan. 2019, pp. 139-150.
4. Valenza G, Greco A, Gentili C, Lanata A, Sebastiani L, Menicucci D, Gemignani A, Scilingo EP.2016 Combining electroencephalographic activity and instantaneous heart rate for assessing brain-heart dynamics during visual emotional elicitation in healthy subjects. Phil. Trans. R.Soc. A 374:20150176.
6. Massimiliano de Zambotti, PhD, John Trinder, PhD, Alessandro Silvani, MD, Ian Colrain, PhD, Fiona C. Baker, PhD, Dynamic coupling between the central and autonomic nervous systems during sleep: a review, Neurosci Biobehav Rev. Jul. 2018; 90: 84-103.
6. Scott D. Rothenberger, Robert T. Krafty, Briana J. Taylor, Matthew R. Cribbet, Julian F. Thayer, Daniel J. Buysse, Howard M. Kravitz, Evan D. Buysse and Martica H. Hall; Time-varying correlations between delta EEG power and heart rate variability in midlife women: The SWAN Sleep Study, Psychophysiology Apr. 2015; 52(4): 572-584.
Japanese Notice of Reasons for Refusal dated May 10, 2022 for corresponding Japanese patent application 2020-502098.
Japanese Notice of Reasons for Refusal dated May 10, 2022 for corresponding Japanese patent application 2020-502098. English Machine Translation.

* cited by examiner

SLOW WAVE ACTIVITY OPTIMIZATION BASED ON DOMINANT PERIPHERAL NERVOUS SYSTEM OSCILLATIONS

FEDERALLY-SPONSORED RESEARCH AND DEVELOPMENT

This invention was made with government support from the National Institute On Alcohol Abuse And Alcoholism of the National Institutes of Health under Award Number U01AA021696, and R21AA024841 and the National Heart, Lung, And Blood Institute of the National Institutes of Health under Award Number R01HL103688. The government has certain rights in the invention.

RELATED APPLICATION DATA

U.S. Provisional application No. 62/533,299 filed on Jul. 17, 2017.

OVERVIEW

Sleep is a fundamental human need, essential for optimal physical and mental health. Sleep is a complex physiological process involving multiple biological systems, fundamental for the health of an individual. It is typically defined as a central nervous system (CNS) phenomenon in which the state of cortical electroencephalographic (EEG) activation determines the individual's state of consciousness. Among the several important EEG rhythms, EEG slow wave activity (SWA) plays a main role in sleep homeostasis, health and disease, and cognitive processing. In fact, insufficient or altered nocturnal distribution patterns of SWA are associated with several diseases and conditions.

SUMMARY OF THE INVENTION

The present invention is directed to overcoming the above-mentioned challenges and others related to slow wave activity (SWA) optimization.

Various aspects of the present disclosure are directed to apparatuses and methods thereof that can be used for maximizing and/or optimizing SWA generation based on features of dominant peripheral nervous system (PNS) oscillations as a function of sleep stages and time. The methodology can include determining optimal windows for delivering stimulation to a user based on the dominant PNS oscillations. The apparatus can form part of a closed-loop stimulation system in which feedback indicative of the user response to the stimulation is used to revise the optimal windows.

In various specific embodiments, a method for enhancing EEG SWA includes receiving one or more bio-signals from a user, such as peripheral or PNS bio-signals including beat-to-beat blood pressure (BP), heart rate (HR), pulse pressure (PP), and pre-ejection period (PEP) from impedance cardiography (ICG), and, optionally deriving EEG signals and/or other CNS signals. The bio-signals can include, but are not limited to, autonomic nervous system (ANS) and cardiovascular (CV) rhythms. Example bio-signals include BP, HR, breathing, photoplethysmographic (PPG) measures, and ICG measures. One or more of the PNS bio-signals may be combined with CNS bio-signals and are used to classify sleep stages of the user. For example, sleep stages can be classified by processing one or more PNS bio-signals, such as by using muscle activity in combination with photoplethysmographic (PPG)-derived HR variability (HRV) measures, or using user behavior (e.g., motion) in combination with EEG and electrooculographic (EOG) signals, and HRV measures.

Dominant oscillations in the PNS, herein referred to as dominant PNS oscillations, are determined based on one or more of the bio-signals and as a function of time and stage of sleep. For example, a PNS bio-signal can be decomposed into a dominant frequency of interest to determine a dominant PNS oscillation. At least one property of the dominant PNS oscillation is characterized, which can include a phase, a phase shift, an amplitude, and/or frequency of the dominant PNS oscillation. The properties of the dominant PNS oscillations can include or be indicative of dominant rhythms across one or more PNS bio-signals, redundancies among rhythms of different PNS bio-signals, and/or phase shifts (e.g., with multiple biorhythms).

The method further includes providing an indication of an optimal window for maximizing SWA generation based on the phase, the phase shift, the amplitude, or the frequency of the dominant PNS oscillation(s). As a specific example, the phase or phase shift of the dominant PNS oscillation is used to determine optimal windows, e.g., regions of interest or time windows, for stimulation and for maximizing EEG SWA within a particular user. The indication is provided to stimulation circuitry that can deliver stimulation to the user within the optimal window. The optimal window can be for one or a combination of ANS and CV rhythms and/or other bio-signals.

Feedback can be provided responsive to the stimulation, which can be based on an EEG signal of the user. The feedback can be used to adapt and optimize timing of the stimulation. For example, the timing of the stimulation can be adapted and optimized according to the phase of dominant PNS oscillations based on the feedback and/or to maximize EEG SWA (e.g., EEG delta power) and/or to modulate proprieties of other EEG frequencies of interest (e.g., increase spindle density, and/or amplitude, and/or power) for the particular user. In a number of embodiments, the method further includes providing pre-stimulation of the PNS, and which can be optimized based on the feedback. The pre-stimulation includes providing peripheral neuromodulation (e.g., transcutaneous vagus nerve stimulation) according to phases of the dominant PNS oscillations to optimize a state of the PNS prior to the (targeted) stimulation to maximize its effect (e.g., SWA enhancement).

In accordance with a number of embodiments, the above-described method can be provided by non-transitory computer-readable storage medium. For example, the computer-readable storage medium has stored thereon program instructions executable by processing circuitry to perform the method.

Various specific embodiments are directed to an apparatus that includes data transmission circuitry and processing circuitry. The data transmission circuitry receives bio-signals, such as central nervous system (CNS) bio-signals and PNS bio-signals, obtained from a user by sensor circuitry having one or more bio-sensors. The data transmission circuitry can be in wired or wireless communication with the one or more bio-sensors. The bio-sensors can obtain the bio-signals and output signals indicative of the ANS state and/or the CNS state of the user.

The processing circuitry can classify a plurality of sleep stages using one or more of the PNS bio-signals, and can characterize properties of dominant PNS oscillations as a function of time (of the night) and the sleep stages using one or more of the PNS bio-signals. For example, the processing circuitry can classify sleep stages by extracting EEG features from an EEG signal and/or extracting other physiological features from the one or more PNS bio-signals, and user behavior (e.g., motion). The properties of the dominant PNS oscillations can include a phase, an amplitude, and/or a frequency of the PNS bio-signals. The processing circuitry determines optimal windows based on the phase and/or other properties of the dominant PNS oscillation where a stimulation or series of stimulations is characterized as improving (e.g., would maximize) EEG SWA and/or other EEG rhythms of interest (e.g., increase in spindle activity) within the user. In various embodiments, the optimal windows can be based on a combination of features, e.g., PNS bio-signals and/or properties thereof. The data transmission circuitry can output an indication of the determined optimal windows to stimulation circuitry that can deliver stimulation to the user within at least one of determined optimized windows for maximizing EEG SWA generation.

In various specific embodiments, the apparatus further includes feedback circuitry that provides a feedback signal indicative of user response to the stimulation based on an EEG signal. The processing circuitry can be arranged with the feedback circuitry to improve EEG SWA generation, other EEG rhythms (e.g., activity within the sigma frequency range, 12-15 Hz) and CNS measures of cerebral hemodynamics (e.g., blood flow velocity as detected by Transcranial Doppler Sonography, oscillation in cerebral hemodynamics as detected by Near-Infrared Spectroscopy), peripheral CV function, and/or other specific oscillatory rhythms based on the feedback signal. For example, the feedback circuitry can improve CV function, or other features of PNS (e.g., high-frequency HRV) and/or CNS (e.g., specific EEG rhythms like spindles' activity, cerebral perfusion) measures based on the feedback signal. The apparatus can further include the stimulation circuitry that provides the stimulation, such as at least one of an acoustic stimulation, a haptic stimulation, electrical stimulation and neuromodulation (e.g., vagus nerve stimulation). The stimulation, according to modality, can target different body locations (e.g., ears, stomach, hands) and/or specific nerves termination (e.g., cervical branch of the vagus nerve). In related and specific embodiments, the processing circuitry can include data processing circuitry and the feedback circuitry. The data processing circuitry determines the optimal windows and adjusts the optimal windows based on the feedback signal. For example, the processing circuitry can optimize EEG SWA generation, for instance, by quantifying spectral analysis of an EEG signal within a frequency of interest (e.g., less than 4 Hz).

In other specific embodiments, the apparatus further includes the sensor circuitry having the one or more bio-sensors used to obtain the bio-signals (e.g., the PNS bio-signals and CNS bio-signals) from the user. The sensor circuitry can include at least two bio-sensors that obtain different types of bio-signals, such as different PNS bio-signals, CNS bio-signals, and other signals. For example, the sensor circuitry can include a sensor that obtains the EEG signal used to derive the feedback signal. The processing circuitry can determine the optimal windows responsive to at least the phase of the dominant PNS oscillations associated with two different types of PNS bio-signals.

Other related and specific embodiments of the present disclosure are directed to an apparatus that includes sensor circuitry and the above-described processing circuitry. The sensor circuitry includes at least two bio-sensors that obtain bio-signals, e.g., PNS bio-signals, CNS bio-signals and/or signals indicative of sleep stages from a user, and provide output signals indicative of an ANS state and/or a CNS state of the user. The processing circuitry classifies a plurality of sleep stages using the signals indicative of the sleep stages and determines parameters of the PNS bio-signals (e.g., peaks and/or other events). The processing circuitry further determines dominant PNS oscillations based on the parameters of the PNS bio-signals and as a function of the sleep stages and time, characterizes properties of the dominant PNS oscillations including an amplitude, phase, and frequency of the dominant PNS oscillations, and determines optimal windows for the PNS state and the CNS state responsive to at least the phase of the dominant PNS oscillations. In specific embodiments, the dominant PNS oscillations are determined based on dominant frequencies associated with parameters of the PNS bio-signals, such as frequencies of the PNS bio-signals during N2 and N3 stages of sleep, although embodiments are not so limited. The apparatus further includes stimulation circuitry that delivers stimulation to the user within at least one of the optimal windows for maximizing EEG SWA generation and feedback circuitry. The feedback circuitry provides a feedback signal to the processing circuitry, the feedback signal being indicative of a user response to the stimulation based on an EEG signal of the user, and the processing circuitry adjusts the optimized window based on the feedback signal. In specific embodiments, the sensor circuitry of above-described apparatus can further include the EEG sensor that provides the EEG signal to the feedback circuitry.

In a specific embodiment, the sensor circuitry can include a BP sensor that provides a signal indicative of beat-to-beat BP. The processing circuitry can determine the dominant PNS oscillations as the function of the sleep stages and time by detecting peaks in BP (e.g., systolic, mean and diastolic peaks) using the signal indicative of BP, determining a dominant frequency of interest based on the detected peaks, decomposing the signal indicative of BP in the dominant frequency of interest, and determining the optimal windows for stimulation based on the decomposed signal indicative of BP in the dominant frequency of interest.

Embodiments in accordance with the present disclosure include all combinations of the recited particular embodiments. Further embodiments and the full scope of applicability of the invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

BRIEF DESCRIPTION OF THE DRAWINGS

Various example embodiments may be more completely understood in consideration of the following detailed description in connection with the accompanying drawings, in which.

Figure 1A:
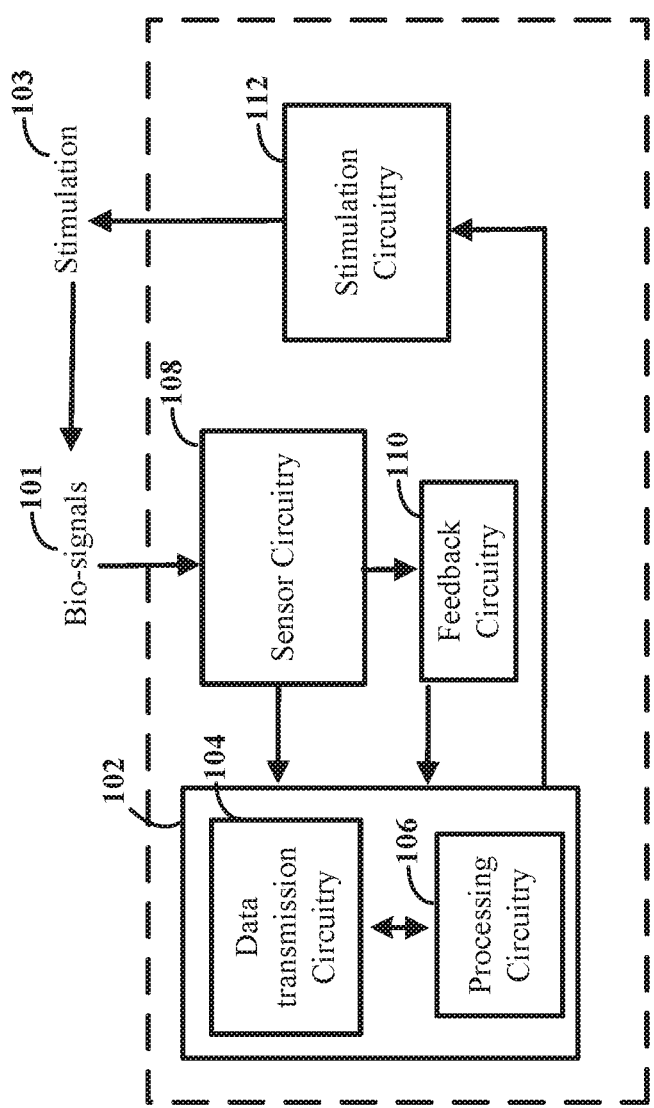
FIGS. 1A-1B illustrate examples of apparatus, in accordance with various embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to variety of apparatuses used for maximizing slow wave activity (SWA) generation based on dominant peripheral nervous system (PNS) oscillations as a function of sleep stages. In certain implementations, the apparatus is used to provide optimal windows for stimulation for SWA generation based on a phase, phase shift, amplitude, or frequency of the dominant PNS oscillations. In some specific implementations, the above-described apparatus and/or method include a closed-loop stimulation system in which feedback indicative of a particular user response to stimulation during an optimal window is used for further revised timing of the stimulations and maximize SWA generation for the particular user. While the present invention is not necessarily limited to such applications, various aspects of the invention may be appreciated through a discussion of various examples using this context.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element.

Various embodiments in accordance with the present disclosure are directed to a technique of enhancing SWA of a user by providing stimulation to a user during optimal windows that are determined based on dominant PNS oscillations as a function time (of night) and sleep stages. As previously described, while sleep is mainly defined based on the state of cortical activation, sleep can be broadly viewed as a coordinated cascade of events occurring in several bio-domains. For example, there is a dynamic coordination between oscillations in central nervous system (CNS) and autonomic nervous system (ANS) and their interplay across the night. During sleep, a biological system undergoes reorganization and restoration. In a healthy system, biorhythms harmoniously manifest and interact with each other. During sleep, CNS cortical activity gradually synchronizes resulting in high-voltage, slow frequency electroencephalogram (EEG) waves, pronounced in the deepest stage of non-rapid-eyes-movement (NREM) sleep, slow wave sleep (SWS). This pattern cyclically alternates with periods of low voltage, mixed frequency EEG combined with muscle atonia and rapid eye movements (REM), characterizing REM sleep. In association with the distinct EEG patterns that characterize the different sleep stages, there are also coordinated patterns in ANS and cardiovascular (CV) indices (e.g., increases in EEG SWA, also called delta power) which are associated with increases in high frequency heart rate variability (HRV) activity.

EEG SWA has a role in sleep homeostasis, health and disease, and cognitive functioning (e.g., memory consolidation). Insufficient or altered nocturnal distribution patterns of SWA are associated with several diseases and conditions (e.g., insomnia, major depressive disorder, Alzheimer's disease and related disorders). Enhancing SWA via EEG, such as via non-invasive auditory stimulation (e.g., pulses of pink noises) can be useful for such health purposes and treating disease. It has been shown that phase-locking the timing of acoustic stimuli to the phases of slow oscillations (SOs, <1 Hz) can be beneficial for SWA enhancement and the related enhancement of sleep dependent memory consolidation. Embodiments in accordance with the present disclosure are directed to enhancing EEG SWA during sleep in humans using closed-loop stimulation timed according to specific oscillatory peripheral rhythms, referred to as PNS oscillations, such as oscillations in the ANS and CV system. Various embodiments are related to CNS-ANS coupling, and specifically on the existence of optimal windows across phases of dominant PNS oscillations in which the stimulation is more effective in generating SWA, such as a function of time and sleep stages. Targeting these windows can maximize SWA enhancement.

A number of related embodiments are related to EEG-based methods for SWA enhancement that target one or more additional measures reflecting sleep restoration (e.g., heart rate variability, blood pressure, heart rate, and breathing). Example methods can be used to manipulate CV rhythms given that slow wave generation following peripheral stimulation is associated with specific fluctuations in CV rhythms (e.g., biphasic cardiac oscillations in response to tone-elicited EEG slow oscillation).

In specific embodiments, a method for enhancing SWA includes receiving one or more bio-signals from a user. The bio-signals can be related to the ANS and CV rhythms, but are not so limited. Bio-signals include PNS-related bio-signals and CNS-related bio-signals, herein referred to as PNS bio-signals and CNS bio-signals. Example PNS bio-signals include signals indicative of blood pressure (BP), heartrate (HR), breathing, photoplethysmogram (PPG) measures, and impedance cardiography (ICG) measures. In specific embodiments, the bio-signals include beat-to-beat BP, HR, and/or pre-ejection period (PEP) from impedance cardiography (ICG), among other signals.

The bio-signals can be processed for enhancing SWA. For example, sleep stages can be classified using one or more of the bio-signals, such as using PNS bio-signals. Sleep stages can be classified by using indication of user behavior (e.g., motion) in combination with PPG-derived HR variability (HRV) measures or using motion in combination with EEG and electrooculographic (EOG) signals. In some embodiments, stimulation can be targeted during specific sleep periods for stimulation across the night (e.g., N2 and/or N3 sleep). Sleep can be assessed using EEG-based methods and/or actigraphy (motion detected in the subject) in combination with other bio-signals (e.g., HR and its variability, skin conductance and temperature). Real-time extraction of EEG features alone and/or in combination with other physiological features (e.g., eye movement, muscle tone, motion, HR and its variability) can be used to classify sleep stages in real time (wake, N1, N2, N3, or REM).

The method can further include determining dominant PNS oscillations based on one or more of the bio-signals as a function of time (e.g., time of night) and the sleep stages. For example, a PNS bio-signal can be decomposed in a dominant frequency of interest which is determined using parameters of the PNS bio-signals, such as peaks or other events. This can be used for determining timing, e.g., optimal windows, for peripheral stimulation. In specific embodiments, the method further includes characterizing at least one property of the dominant PNS oscillations, including a phase, a phase shift, an amplitude, and/or a frequency of the dominant PNS oscillations. Sleep can be accompanied by fluctuations in several bio-rhythms, such as breathing, HRV, in response to breathing and to other events, BP, and/or pulse waves. The dominant frequency in these rhythms as well as other features (e.g., amplitude) can vary as a function of sleep stage and time, between and within-individuals. The method allows for real-time estimation of the features of these oscillations. The properties characterize such dominant rhythms, e.g., the amplitude, phase, and/or frequency, across one or more of the bio-signals, redundancy among bio-signals, and phase shifts.

An indication of an optimal window or windows for maximizing SWA generation can be determined and provided to stimulation circuitry and based on the phase, the phase shift, the amplitude and/or the frequency of the dominant PNS oscillations. The stimulation circuitry can deliver stimulation to the user within at least one of the optimal windows. As a specific example, the phase or phase shift of the dominant PNS oscillation can be used to determine the optimal windows for delivering stimulation to the user and for maximizing EEG SWA within the user.

In specific embodiments, different parameters from several bio-signals are obtained and include, but are not limited to, systolic (SBP), diastolic (DBP), and mean (MBP) BP, peaks in inspiration/expiration, inter-beat-intervals (IBIs), pulse pressure (PP), pre-ejection period (PEP), pulse transit time (PTT), pulse arrival time (PAT), which can be derived from streaming bio-signals using automatic detection algorithms. Example algorithms involve adaptive segmentation, noise and artifact detection, envelope detection, multi-stage spectral HR detection, scaling and normalization, outlier removal, and autoregressive modeling. To estimate the CV dominant frequencies and their corresponding phases and amplitudes, as a specific example, the power spectral density (PSD) of the last two minutes (e.g., time can be adjusted) is calculated. The PSD is smoothed, and the dominant frequencies are detected using a peak detection algorithm where the most dominant peaks are detected and ranked according to their prominence. The prominence of the peaks is defined based on how much the peak stands out due to their intrinsic height and their location relative to other peaks. The respiration frequency is first estimated as the most prominent peak between 0.15 to 0.4 Hz. The search for the rest of the dominant peaks is limited between 0.02 Hz and the estimated respiration frequency. In order the calculate the instantaneous phases and amplitudes corresponding to each dominant frequency, filters with narrow pass-bands are designed and applied to the corresponding cardiovascular signals to filter out all the unwanted frequency content other than the frequency of interest. Hilbert transform is applied to the filtered waveforms to calculate their instantaneous amplitudes, frequencies and phases. Based on the derived instantaneous phases, the filtered cardiovascular signals are segmented into several optimal window, e.g., regions of interest (ROIs), where the peripheral stimulations are to be applied.

The instantaneous amplitudes, frequencies, and phases may be also extracted in real-time using an adaptive tracking algorithm such as Kalman or particle filters. A measurement model is defined for the observed bio-signals as the addition/multiplication of several harmonically related sinusoidal functions. Each sinusoidal function represents a major frequency component of the bio-signals and includes three parameters: instantaneous amplitude, frequency, and phase. Other variations of the bio-signals can be modeled using a slow varying component, an impulsive noise component, and a white noise component. The parameters of the model including all the instantaneous frequencies, phases, and amplitudes form the states of the system that are modeled using an autoregressive moving average (ARMA) or autoregressive integrated moving average (ARIMA) models. The parameters of the state model are adaptively estimated and tracked using a Bayesian approach by constructing the posterior probability density function (PDF) of the state base on all available measurements. A recursive filtering approach can be used for this purpose that consists of two stages: prediction and update. In the prediction stage, the system model is used to predict the state PDF from one measurement time to the next. In the update stage, the prediction PDF is modified using the latest measurements. Such an approach can be more robust to dynamic changes in the system. The initial values of the model parameters can be obtained by analyzing the PSD main frequency components within a prior window as explained earlier. The adaptive filter parameters can be reinitialized at each sleep stage for better adaption to the physiological variabilities.

As a specific example using BP, BP measurements are obtained using a BP sensor and provided to processing circuitry. The processing circuitry determines the dominant PNS oscillations as the function of sleep stages and time by detecting peaks in BP using the bio-signal indicative of BP, determining one or more dominant frequencies of interest based on the detected peaks, and decomposing the bio-signal indicative of BP in the dominant frequency of interest. Using the decomposed bio-signal, optimal windows for stimulation can be determined. Although the specific example described BP measurements, the optimal window(s) can be for at least one of an ANS, CV rhythm, and other bio-signals. In some specific embodiments, the optimal window(s) can be the results of a combinations of properties of a bio-signal or more than one bio-signal.

The method can further include providing feedback responsive to the stimulation based on an EEG signal obtained from the user. Based on the feedback, the method includes adapting and optimizing the timing of the stimulation, such as according to the phase of the dominant PNS oscillation. The feedback is therefor used to maximize SWA generations, such as EEG delta power. The optimal window is updated using the feedback. In specific embodiments, the feedback can include quantifying SWA which is feedback in the closed-loop stimulation system and used to assess the efficiency of the whole system. As previously described, a main goal of the apparatus can be to maximize EEG SWA, although embodiments are not so limited. SWA can be quantified in real time by spectral analysis of the EEG signal within the frequencies of interest (<4 Hz). However, the apparatus is not limited to the enhancement of SWA and can also or alternatively target enhancement of cardiac function (e.g., HRV), specific oscillatory rhythms or other parameters known to reflect restorative sleep, and/or maximize a combination of measures.

In various specific embodiments, the method further includes providing pre-stimulation of the PNS. The pre-stimulation can include providing peripheral neuromodulations, such as transcutaneous vagus nerve stimulation, according to a phase of one or more dominant PNS oscillations and to optimize a state of the PNS prior to providing the stimulation for maximizing SWA enhancement.

The above-described method can be implemented by an apparatus having data transmission circuitry and processing circuitry. The data transmission circuitry receives the bio-signals as obtained from a user and by sensor circuitry having one or more bio-sensors. The bio-signals can include PNS bio-signals and CNS bio-signals. The data transmission circuity can communicate with the bio-sensors in a wired or wireless manner. The processing circuitry can classify the plurality of sleep stages, characterize properties of the dominant PNS oscillation as a function of time and sleep stages, and determine the optimal windows on the phase and/or other properties, and communicate the same to the data transmission circuitry. The data transmission circuitry can further output an indication of the optimal window to stimulation circuitry that delivers stimulation to the user within the optimal window for maximizing EEG SWA generation. The apparatus can further include feedback circuitry used to provide a feedback signal to indicate a user response to the stimulation based on an EEG signal obtained from the user. The feedback signal can indicate an amount of SWA that is generated responsive to the stimulation. The feedback signal can be used to adjust the optimal window(s), such as for further maximizing the EEG SWA generation and/or to improve other functions, such as improving central hemodynamics, CV function or specific oscillatory rhythms.

In a number of specific embodiments, the apparatus further includes the sensor circuitry having one or more bio-sensors. The bio-sensors obtain the bio-signals, including PNS bio-signals and signals indicative of sleep stages and can output signals indicative of an ANS state and CNS state of the user. In some specific embodiments, the bio-sensors include an EEG sensor that provides an EEG signal, and which can be provided to the feedback circuitry for deriving the feedback signal.

As a specific example, an apparatus includes sensor circuitry, processing circuitry, stimulation circuitry, and feedback circuitry. The sensor circuitry includes two or more bio-sensors that obtain the bio-signals, which include PNS bio-signals, CNS bio-signals and/or signals indicative of sleep stages, from a user and provide output signals indicative of an ANS state and/or a CNS state of the user. The processing circuitry classifies a plurality of sleep stages using the signals indicative of the sleep stages, determines parameters (e.g., peaks or other events) of the PNS bio-signals, determines dominant PNS oscillations based on the parameters and as a function of the sleep stages and time, characterizes properties of the dominant PNS oscillations including an amplitude, phase, and frequency of the dominant PNS oscillations, and determines optimal windows for the PNS state and the CNS state responsive to at least the phase of the dominant PNS oscillations. In specific embodiments, the processing circuitry determines the dominant PNS oscillations based on dominant frequencies associated with the parameters of the PNS bio-signals, such as frequencies of the PNS bio-signals during N2 and N3 stages. The stimulation circuitry delivers stimulation to the user within at least one of the optimal windows for maximizing EEG SWA generation. The feedback circuitry provides a feedback signal to the processing circuitry, the feedback signal being indicative of a user response to the stimulation based on an EEG signal of the user, and the processing circuitry is further adjust the optimized window based on the feedback signal. In some embodiments, the feedback circuitry can include a specific component of the processing circuitry, although embodiments are not so limited.

In other embodiments, the methods disclosed for enhancing SWA can also be used to optimize specific EEG parameters to further bring about beneficial effects. Examples of EEG measurable parameter to target for maximizing restorative sleep and/or enhancing specific biological processes (e.g. memory consolidation), can include but not is not limited to increasing the absolute value of an index, regulating amplitude and phase of oscillations (e.g. EEG spindle activity), alone or in combination central (e.g. central hemodynamics such as blood flow velocity, oscillations in cerebral hemodynamics, etc.) or peripheral (e.g. indices blood pressure fluctuations, cardiac function, etc.) bio-signal properties.

Figure 1B:
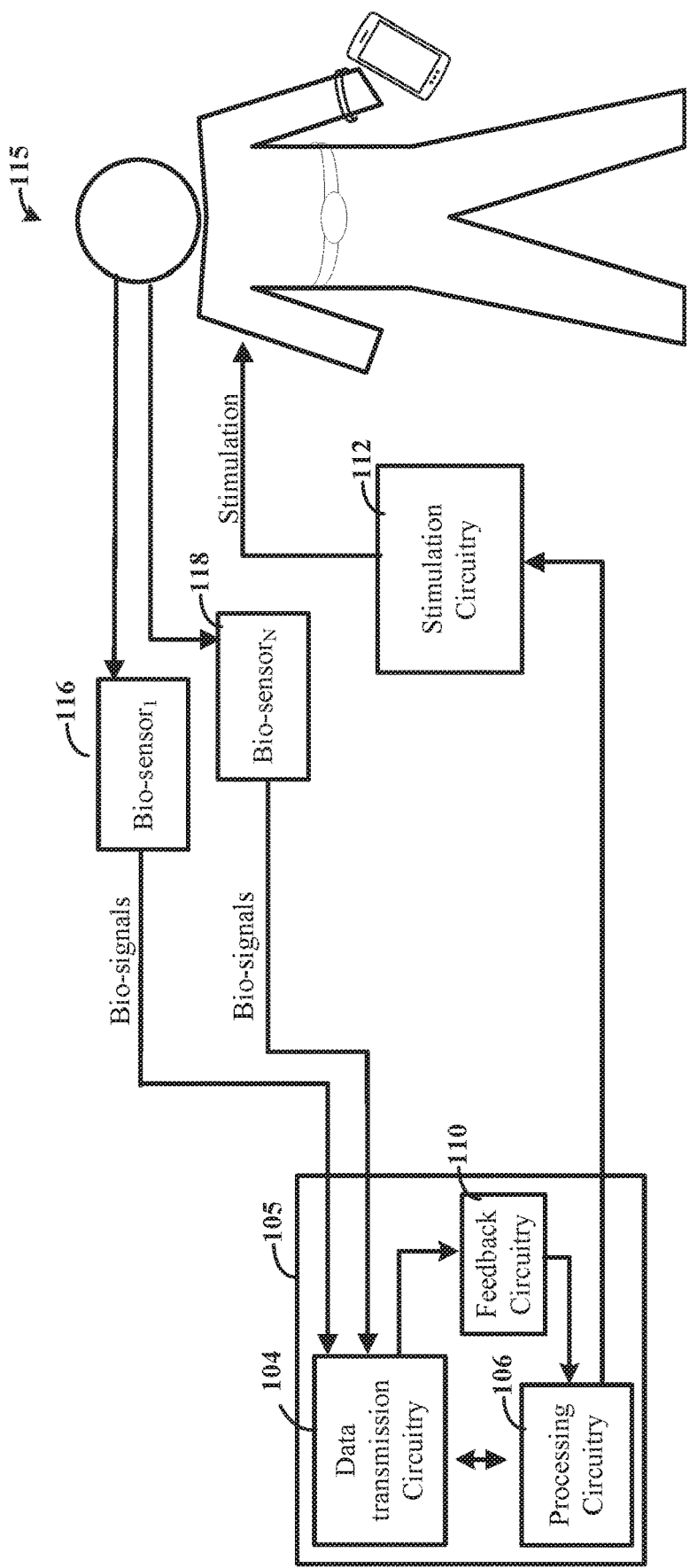

Turning now to the figures, FIGS. 1A-1B illustrate examples of an apparatus, in accordance with various embodiments. Various embodiments and apparatuses are used for enhancing SWA generation by sleep regulatory systems, such as the human body.

Sleep regulatory systems can be closely associated, anatomically and physiologically, with the ANS. The ANS regulates the majority of the body's internal processes (e.g., blood pressure, myocardial function, breathing, body temperature, digestion, urination) via afferent and efferent sympathetic and parasympathetic pathways, allowing adaptive responses to internal and external stressors, guaranteeing the body homeostatic milieu.

Measures reflecting ANS function can fluctuate across a night of sleep, depending on both homeostatic (e.g., related to the duration of sleep and of prior wakefulness) and circadian processes, together with EEG oscillations, and in association with phasic events during sleep. These interactions reflect the dynamic interplay between the CNS and the ANS.

FIG. 1A illustrates an example of apparatus that performs SWA enhancement. The apparatus includes at least data transmission circuitry 104 and processing circuitry 106 used to obtain and process bio-signals obtained from a user and to provide indications of when to stimulate the user to stimulation circuitry 112 for enhancing SWA generation. The data transmission circuitry 104 and processing circuitry 106 can be part of a computing device 102, such as a data processing computer. The data transmission circuitry 104 receives bio-signals 101 from sensor circuitry 108, such as PNS bio-signals, CNS bio-signals, among others. The data transmission circuitry 104 can be in wired and/or wireless communication with different bio-sensors and/or a sensor circuitry 108 used to aggregate the data from the bio-sensors.

The bio-signals 101 are related to ANS rhythms, CV rhythms, among other signals. In specific embodiments, the bio-signals include PNS bio-signals and CNS bio-signals. Example bio-signals include BP, HR, breathing, PPG measures, EEG measures and ICG measures. In some embodiments, the bio-sensors collect raw physiological data, such as BP and HR, and may further process the data to output bio-signals including beat-to-beat BP, heart rate, and PEP from an ICG.

In various embodiments, the apparatus further includes the sensor circuitry 108 having at least one bio-sensor. The bio-sensor is used to obtain the bio-signals, and can include an EEG sensor, a user wearable devices (e.g., a smart watch, smart glasses, smart clothes, etc.), and/or other user devices, such as a smart bed, which can be worn by or otherwise used by the user when sleeping and obtains the bio-signals. In specific embodiments, the bio-sensors can obtain at least two different types of bio-signals, such as those indicative of PNS and those indicative of CNS and/or two or more different PNS bio-signals.

The data transmission circuitry 104 provides the bio-signals 101 to the processing circuitry 106 for optimizing SWA generation. The processing circuitry 106 receives the bio-signals and processes one or more of the bio-signals for classifying a plurality of sleep stages. The sleep stages can be classified by extracting EEG features from an EEG signal and/or extracting other physiological features from one or more bio-signals, such as EOG, muscle tone, motion, HR, and/or HRV. As such, the bio-signals that are indicative of the sleep stages can be used to classify the same.

The processing circuitry 106 can determine one or more dominant PNS oscillations and properties of the dominant PNS oscillations. For example, the dominant PNS oscillation can be determined using one or more of the bio-signals, e.g., the PNS bio-signals, as a function of time (e.g., time of night) and the sleep stages. Example dominant PNS oscillations include breathing, ANS oscillations, and CV oscillations. The dominant PNS oscillations can be determined based on parameters of the PNS bio-signals, such as peaks or other events in the PNS bio-signals. One or more properties of the dominant PNS oscillations are characterized and which can include or refer to dominant rhythms across one or more bio-signals, redundancy among rhythms of different bio-signals, and phase shifts. In various embodiments, a PNS bio-signal is decomposed in a dominant frequency to determine the dominant PNS oscillation. Example properties of the dominant PNS oscillation include a phase, a phase shift, an amplitude, and a frequency of the dominant PNS oscillation.

The processing circuitry 106 uses the properties of the dominant PNS oscillation(s) to determine optimal window for delivering stimulus to optimize EEG SWA. For example, the phase and/or other properties of the dominant PNS oscillation(s) are used to determine optimal windows where a stimulus or series of stimulations is anticipated (e.g., would) or is otherwise characterized as improving or maximizing EEG SWA within the user.

In some embodiments, the optimal windows are for more than one property of a bio-signal and/or for properties of more than one bio-signal. For example, the processing circuitry 106 can determine the optimal windows responsive to the properties of two or more dominant PNS oscillations, such as using the phases associated with two or more PNS bio-signals. In a specific embodiment, the optimal windows are for the PNS state and the CNS state, such as ROIs that overlap with both the PNS and CNS states.

The optimal windows can be communicated to stimulation circuitry 112. For example, the data transmission circuitry 104 outputs an indication or signal indicative of the determined optimal windows to the stimulation circuitry 112. The stimulation circuitry 112, which may form part of the apparatus in some specific embodiments, is configured to deliver the stimulation 103 or series of stimulations to the user within at least one of the optimal windows for maximizing EEG SWA generation. The stimulation circuitry 112 can provide peripheral stimulation and/or can include or be referred to as PNS stimulation circuitry. Peripheral stimulation can involve the use of different methods, including but not limited to transcranial direct current stimulation, transcranial magnetic stimulation, acoustic stimulation, haptic stimulation, electrical stimulation and neuromodulation (e.g., vagus nerve stimulation). The stimulation, according to modality, can target different body locations (e.g., ears, stomach, hands) and/or specific nerves termination (e.g., cervical branch of the vagus nerve).

An example of the peripheral stimulation can include, but is not limited to, the use of auditory stimuli of 1,000 Hz presented binaurally at around 60 decibels (dB) for 50 milliseconds (msec) (e.g., 2 msec rise and fall time). Stimuli can be presented alone or in blocks (e.g., 5 pulses). Intensity can be dynamically adjusted to maximize slow wave generation and minimize potential arousal-type of responses measured by increases in EEG alpha rhythm and higher frequencies EEG activity, increase in motion, muscle tone. The refractory periods between stimulations is variable and can be automatically determined by a machine learning algorithm.

Several advantages of using acoustic stimulation include, but are not limited to, reduced system complexity, feasibility, simplicity in the analysis implementation and real time automatization of closed-loops, and absence of interference with the main output variables of interest, as compared to other available methods like the use of electrical stimulation.

In a number of specific embodiments, the stimulation circuitry 112 can provide pre-stimulation of the PNS. Pre-stimulating PNS can include providing peripheral neuromodulations (e.g., transcutaneous vagus nerve stimulation) according to phases of the dominant PNS oscillations to optimize a state of the PNS prior to providing the target stimulation for maximizing SWA enhancement. The data transmission circuitry 104 can communicate the timing of the pre-stimulation based on the determined dominant PNS oscillation and the respective phases, such as to the stimulation circuitry 112.

In various embodiments, the apparatus can form part of a closed-loop stimulation system that includes provided feedback to the system indicative of a user response to stimulation and which is used to further optimize SWA generation and/or other oscillations. For example, the apparatus and/or system can further include feedback circuitry 110 that provides the feedback signal indicative of the user response to the stimulation, such as based on an EEG signal obtained from the user. The feedback signal can include or otherwise be indicative of EEG delta power as a function of the stimulation and, optionally, of other bio-signals. In specific embodiments, the processing circuitry 106 receives the feedback signal, via the data transmission circuitry 104, and processes the same to improve SWA generation by quantifying spectral analysis of the EEG signal within a frequency of interest (e.g., less than 4 Hz) and/or by adjusting the optimal windows based on the EEG delta power. The processing circuitry 106 can, alternatively and/or in addition, use the feedback signal to improve CV function or other specific oscillatory rhythms. In such embodiments, the system can feedback user response to the stimulus, which can include an EEG measure and one or more other bio-signals indicative of CV or other oscillatory rhythms, and uses the same to adjust the optimal windows for further maximizing EEG SWA generation, CV function, and/or for other PNS oscillations. For example, as previously described, the EEG SWA generation can be maximized in combination with (or alternatively) other EEG rhythms (e.g., activity within the sigma frequency range, 12-15 Hz) and CNS measures of cerebral hemodynamics (e.g., blood flow velocity as detected by Transcranial Doppler Sonography, oscillation in cerebral hemodynamics as detected by Near-Infrared Spectroscopy), peripheral CV function, and/or other specific oscillatory rhythms based on the feedback signal.

FIG. 1B illustrate an example of an apparatus, in accordance with various embodiments. The apparatus can include similar components to those illustrated in FIG. 1A, with further details provided. In various embodiments, the sensor circuitry includes a plurality of bio-sensors 116, 118 that obtain PNS bio-signals and CNS bio-signals from a user 115. As illustrated, the bio-sensors 116, 118 may be worn by the user 115 or otherwise in contact with the user 115, such that bio-signals are obtained while the user is sleeping. The bio-sensors may include user wearable devices, such as electrodes used to obtain an EEG signal, smart watch, and other types of devices, such as a smart bed. The bio-sensors may wirelessly (or in a wired manner) communicate data directly to a computing device 105 or to sensor circuitry, such as a smartphone, that aggregates the bio-signals and outputs the same to the computing device 105.

The computing device 105 can include the previously-described data transmission circuitry 104, processing circuitry 106, and optionally the feedback circuitry 110. The processing circuitry 106 processes the bio-signals to determine optimal windows which are communicated to the stimulation circuitry 112 for providing a stimulation or series of stimulations to the user 115. Bio-signals are obtained responsive to the stimulation and provided to the feedback circuitry 110 to provide a feedback signal indicative of the user response and which is used by the processing circuitry 106 for further adjusting the optimal windows for maximizing EEG SWA.

Figure 2:
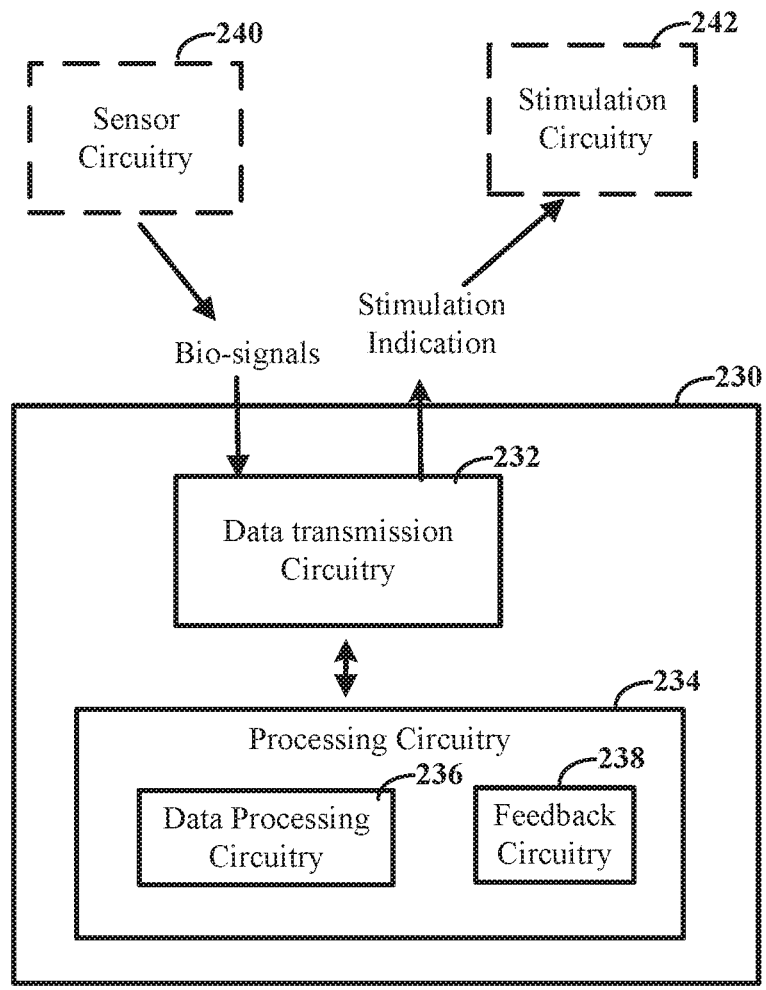
FIG. 2 illustrates an example apparatus used for enhancing slow wave activity, in accordance with various embodiments.

FIG. 2 illustrates an example apparatus used for enhancing SWA, in accordance with various embodiments. The apparatus 230 illustrated by FIG. 2 can include the apparatus described in FIG. 1A and/or the computing device 105 described in FIG. 1B. As illustrated, the apparatus 230 similarly includes the data transmission circuitry 232 which is used to obtain the bio-signals from sensor circuitry 240 and to output an indication of timing for stimulation (e.g., the optimal windows) to stimulation circuitry 242. The data transmission circuitry 232 can obtain bio-signals that are responsive to such stimulation, which is used to generate the feedback signal.

The processing circuitry 234 of the apparatus 230 can include data processing circuitry 236 and the feedback circuitry 238. The data processing circuitry 236 processes the bio-signals to determine the optimal windows, as previously described. The feedback circuitry 238 provides a feedback signal to the data processing circuitry 236 which is indicative of the user response to the stimulation. The feedback signal can include EEG delta power as a function of time and the stimulation, and that is based on an EEG measure of the user, and/or can include additional bio-signals. The data processing circuitry 236 processes the feedback signal by adjusting the optimal windows.

Figure 3A:
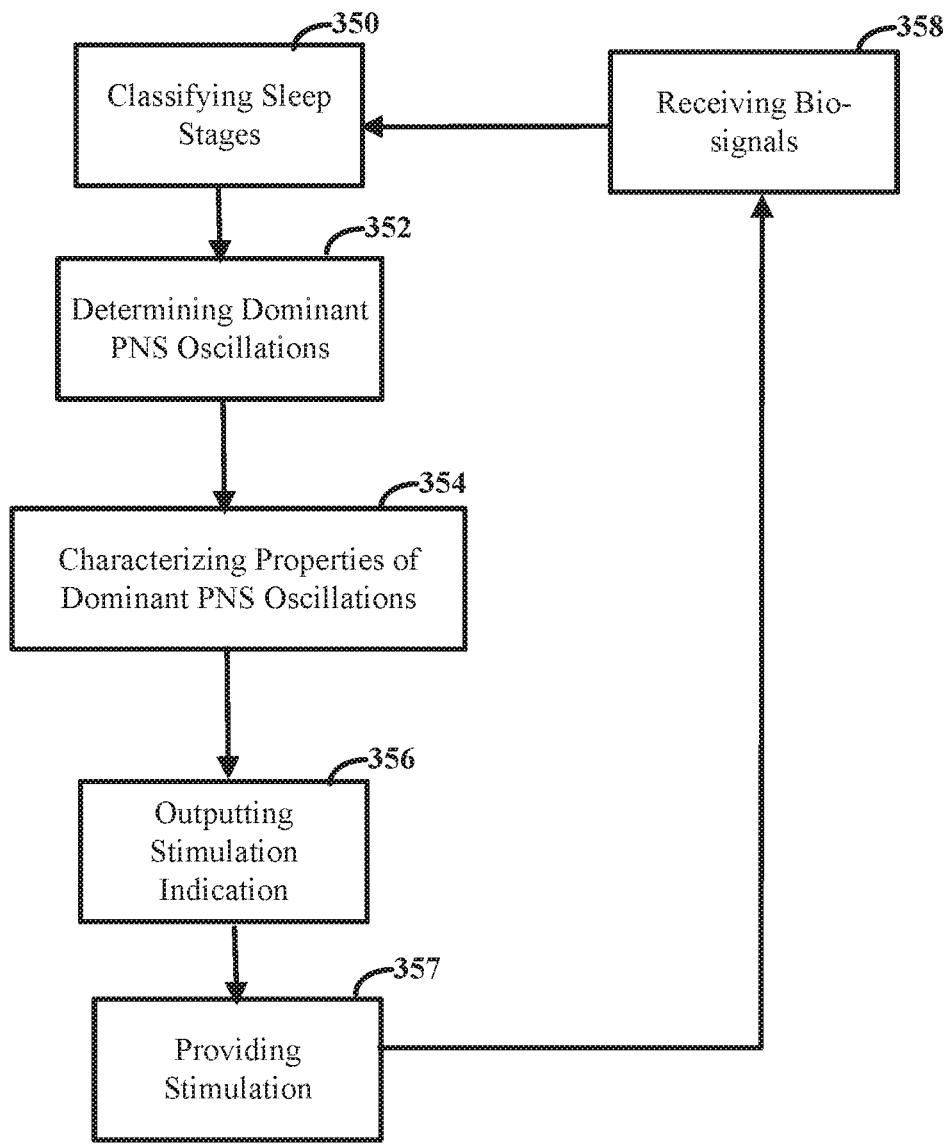
FIGS. 3A-3B illustrate example methods for enhancing slow wave activity, in accordance with various embodiments.
Figure 3B:
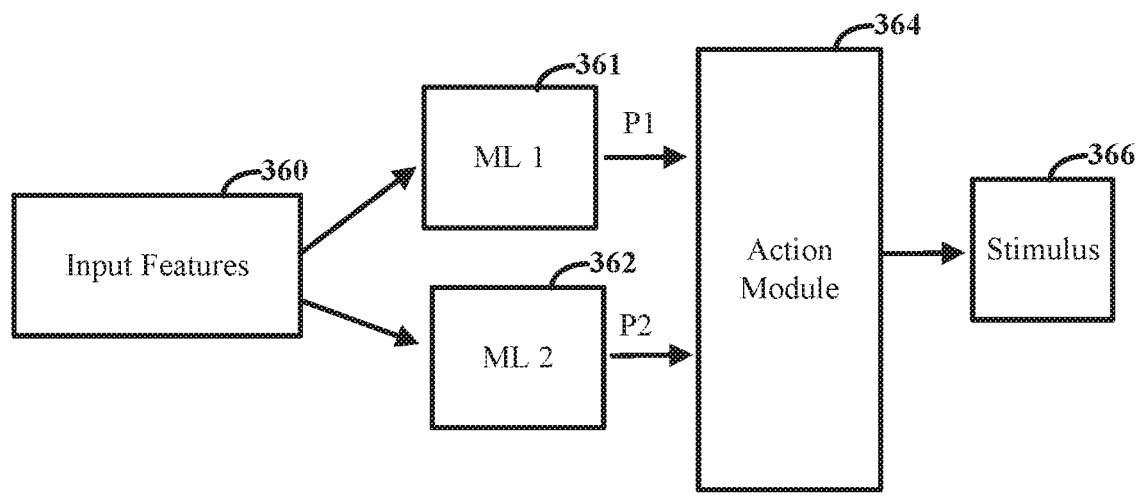

FIGS. 3A-3B illustrate example methods for enhancing SWA, in accordance with various embodiments. FIG. 3A illustrates, for example, a closed-loop stimulation methodology. As illustrated at 358, one or more bio-signals are received. As previously described, such bio-signals can include PNS bio-signals and CNS bio-signals that are indicative of or otherwise related to the ANS and CV rhythms and/or ANS state and CNS state of the user and/or sleep stages. One or more of the bio-signals are used to classify the sleep stages of the user, at 350. In specific embodiments, the sleep stages are classified by processing one or more of the bio-signals (e.g., peripheral or PNS bio-signals) and user behavior, such using motion in combination with a PPG-derived HRV measure and/or using motion in combination with EEG and EOG signals.

The method further includes determining dominant PNS oscillations, at 352, based on the one or more bio-signals, such as one or more PNS bio-signals, and as a function of time and the sleep stages. For example, a PNS bio-signal can be decomposed in a dominant frequency of interest based on a parameter (e.g., peaks or other events) of the PNS bio-signal. At least one property of the dominant PNS oscillations are characterized, at 354. Example properties include a phase, phase shift, amplitude, and frequency, as previously described. Based on the one or more properties, optimal windows can be identified which can be used to optimize EEG SWA generation. The optimal window can be for multiple properties of a dominant PNS oscillation or for one or more property of multiple dominant PNS oscillations associated with more than one type of PNS bio-signal, such as properties, e.g., peaks/events, or parameters, e.g., phase, shifts, amplitude. As a specific example, the phase or phase shift of the dominant PNS oscillation is used to determine the optimal window for delivering stimulation to the user for maximizing EEG SWA generation. As another specific example, the optimal window(s) is for at least one of an ANS rhythm, CV rhythm, and other bio-signals.

At 356, an indication of the one or more optimal windows is output to the stimulation circuitry and the stimulation circuitry provides one or more stimulations during at least one of the optimal windows, at 357. Responsive to the stimulation, at 358, a feedback signal is provided that is indicative of the user response to the stimulation. The feedback signal can be based on one or more obtained bio-signals, such as an EEG and other bio-signals. As previously described, the feedback can be used to adapt and optimize the timing of the stimulation according to the phase of the dominant PNS oscillations and to maximize EEG SWA generation for a particular user (and/or other EEG rhythms of interest (e.g., increase in spindle activity)).

Although not illustrated, various embodiments can include providing pre-stimulations of the PNS. As previous described, the pre-stimulation can be based on the dominant PNS oscillations. For example, a peripheral neuromodulation can be provided to the particular user according to the phases of the dominant PNS oscillations.

FIG. 3B illustrates a specific example of providing feedback which is used for machine learning for a closed-loop peripheral stimulation. Machine learning (ML) modules are designed to learn from the extracted features 360 and predict the variations in the feedback output (e.g., EEG delta power) at every instance of time based on the feature patterns and the presence of a stimulus. Time can be based on seconds or following intrinsic bio-rhythms like the heart beats. Extracted features can include parameters of the bio-signals and/or properties of the dominant PNS oscillations.

The first ML module 361 continuously trains over the extracted features 360 to predict the percentage of the change in the feedback output. Given the EEG delta power as the output measure, the averaged power in the past X seconds is calculated and compared to the averaged power level in the next X seconds (s) (e.g., 2 s, 3 s, 4 s, 5 s, 6 s) and their difference is represented as a percentage, where a positive value represents an increase and a negative value represents a decrease. Although as may be appreciated, embodiments are not limited to using EEG delta power as the output measure, and can include other CNS indices (e.g., EEG spindle activity, cerebral hemodynamics) and bio-signals in combination with EEG delta power and/or in the alternative thereof. The feedback output value which represents the amount of increase or decrease in feedback output level is mapped between −1 to 1 using a sigmoidal transfer function. These values form the ML target value based on which the ML module is trained. The output of the trained ML can also be viewed as a probability value of increase or decrease (based on the output signal) in feedback output level, and which can be provided to the action module 364 for determining an adjustment to the stimulus 366.

In case a stimulus is applied, a second ML module 362 is trained that computes the percentage of the change in the feedback output in accordance to the stimulus presented. The second ML module 362 is trained based on the feedback variations and like the first ML module 361, outputs a value representing the amount of increase or decrease in feedback output level.

The trained second ML module 362 continuously reads the input features and outputs the amount of an increase or decrease in EEG delta power, given a stimulus to be applied. If this value passes a threshold, it can trigger the stimulus 366.

At any time where a stimulus is applied, the second ML module 362 can learn from the input feature and the feedback output level. Similarly, the output is provided to the action module 364 for triggering the stimulus 366.

The first ML module 361 continuously reads the input features and trains based on the feedback output variations. It can also continuously output a value representing an increase or decrease in EEG delta power, given no stimulus is to be applied. If this value is below a threshold, meaning that the power in EEG delta frequencies is going to be significantly decreased, it can also trigger a stimulus 366 via the action module 364.

A specific example of the ML module is a regression model which defines the relationship between the input feature patterns and the amount of change in the feedback output. However embodiments are not so limited and another example is a neural network such as a multi-layer perceptron (MLP) that can find more complex or non-linear relationship between the input features and feedback output variations.

Deep learning methods such as deep neural networks (DNN), convolutional neural networks (CNNs) and long short-term memory (LSTM) may be incorporated in the ML modules to learn from the already extracted features or to extract the most appropriate features from the multichannel physiological signals and find the underlying relationship between the input data and the feedback output variations.

Feature selection methods can be applied for the selection of the best set of features predicting the feedback output variations. Different feature selection methods including filter method, wrapper method, and/or embedded method can be applied for this purpose. The feature selection methods can be applied and tuned per individual or on a general set of data collected from several individuals. The best selected features can then be fed to the above described online MLs.

Since the dimension of the input features can be very high, statistical methods such as principal component analysis or linear discriminant analysis can be used to transform the features into a lower dimension subspace, where a more precise and efficient representation of the input patterns is achieved. Such effective data representation of input data can improve the learning and generalization capability of the learning system. Several analytical techniques (e.g., Granger causality, transfer entropy) may be used to derive information from the dynamic relationships between multiple physiological inputs and use those computational outputs as input variables for the system as well.

FIGS. 4A-4E illustrate an example method for determining the optimal windows for stimulation for enhancing SWA, in accordance with various embodiments. FIGS. 4A-4E illustrate, more specifically, an example of determining dominant PNS oscillations related to BP and as a function of the time of night and sleeps stages. After processing the BP signals, automatic algorithms are used to detect the parameters of the BP signals (e.g., FIG. 4A), determine dominant frequencies (e.g., FIG. 4B), decompose the BP signal into the dominant frequencies (e.g., FIGS. 4C-4D), which is then used to determine the optimal windows for delivering the stimulation (e.g., FIG. 4E).

Figure 4A:
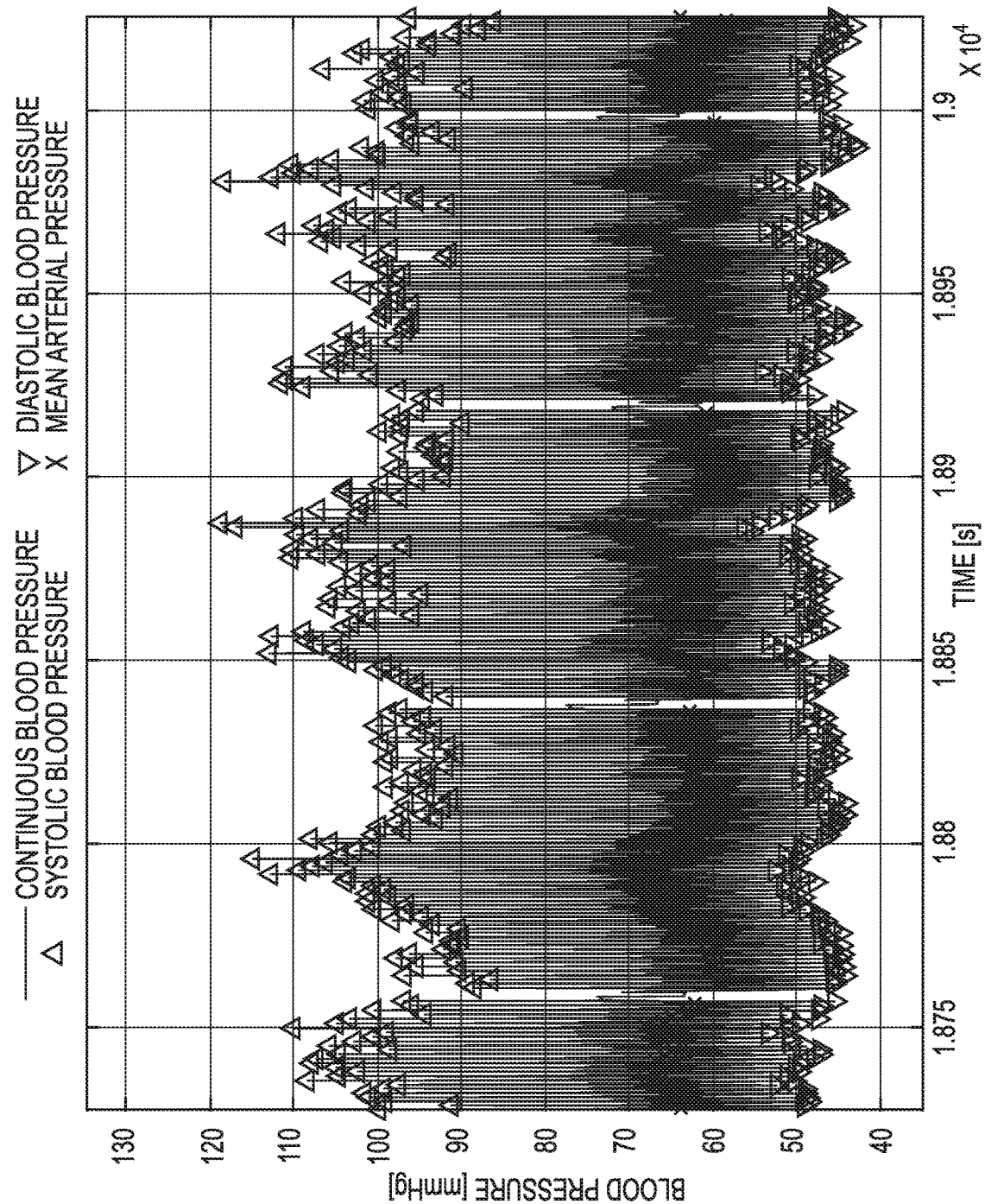
FIG. 4A-4E illustrate an example method for determining the optimal windows for stimulation for enhancing slow wave activity, in accordance with various embodiments.
Figure 4B:
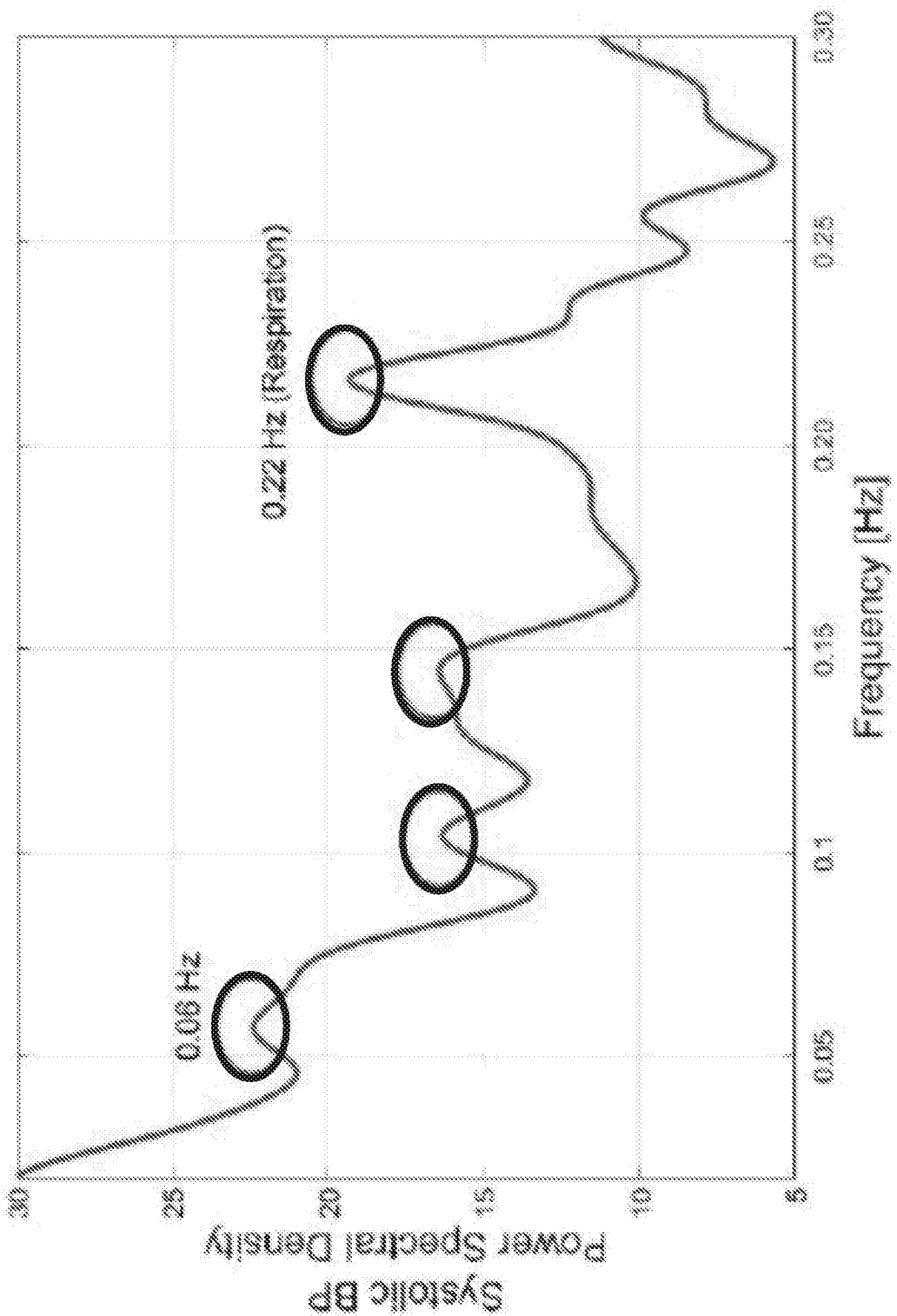
Figure 4C:
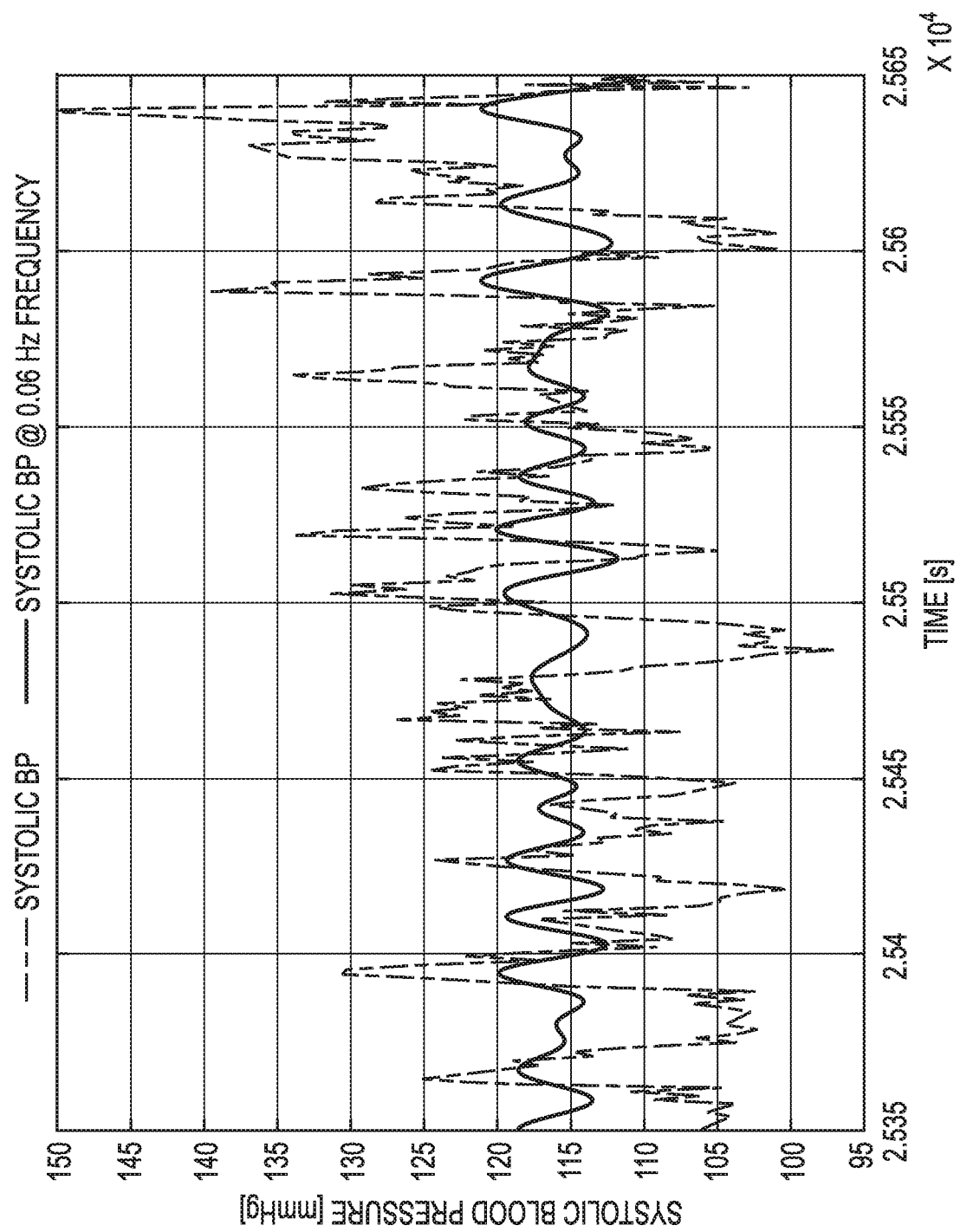
Figure 4D:
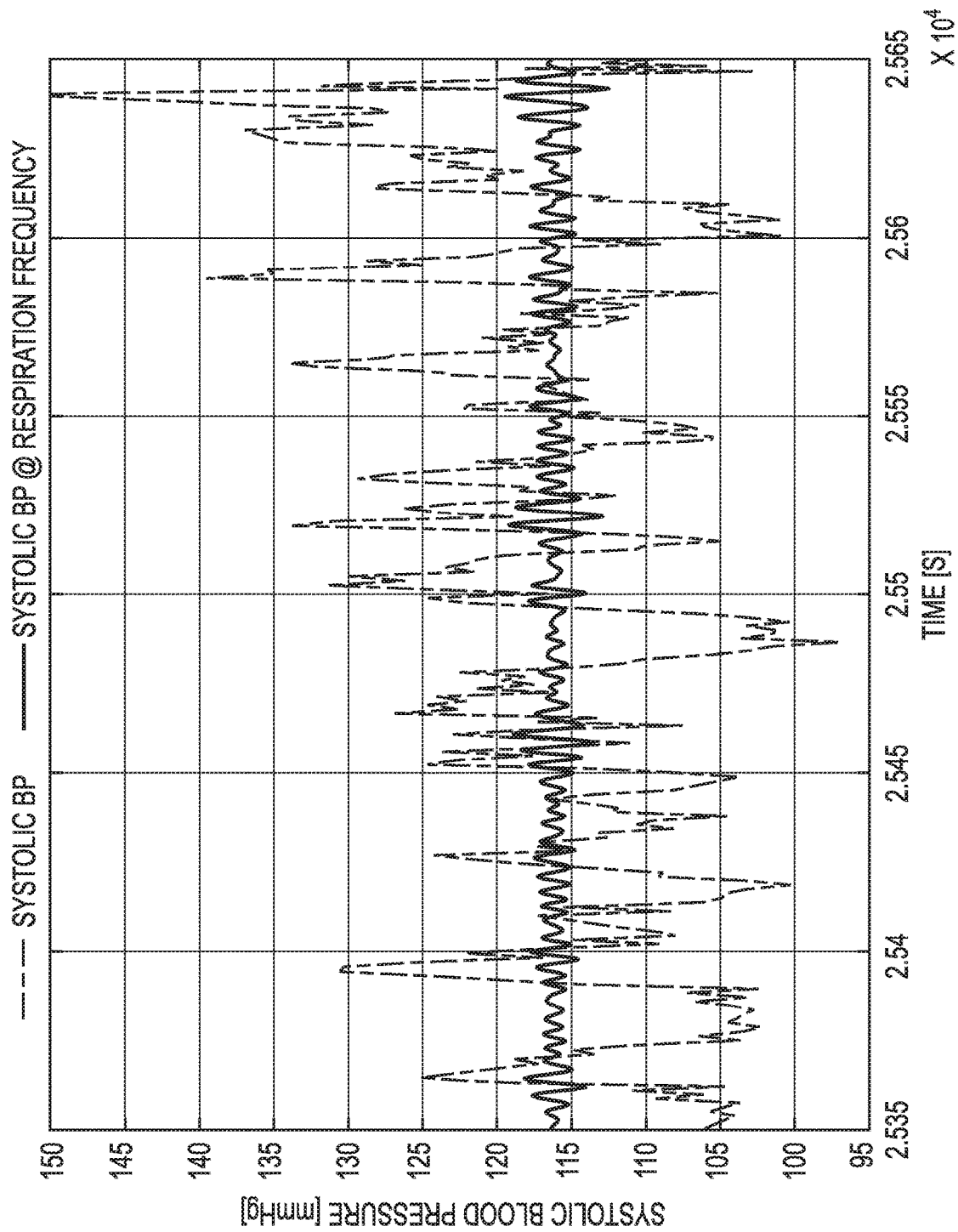
Figure 4E:
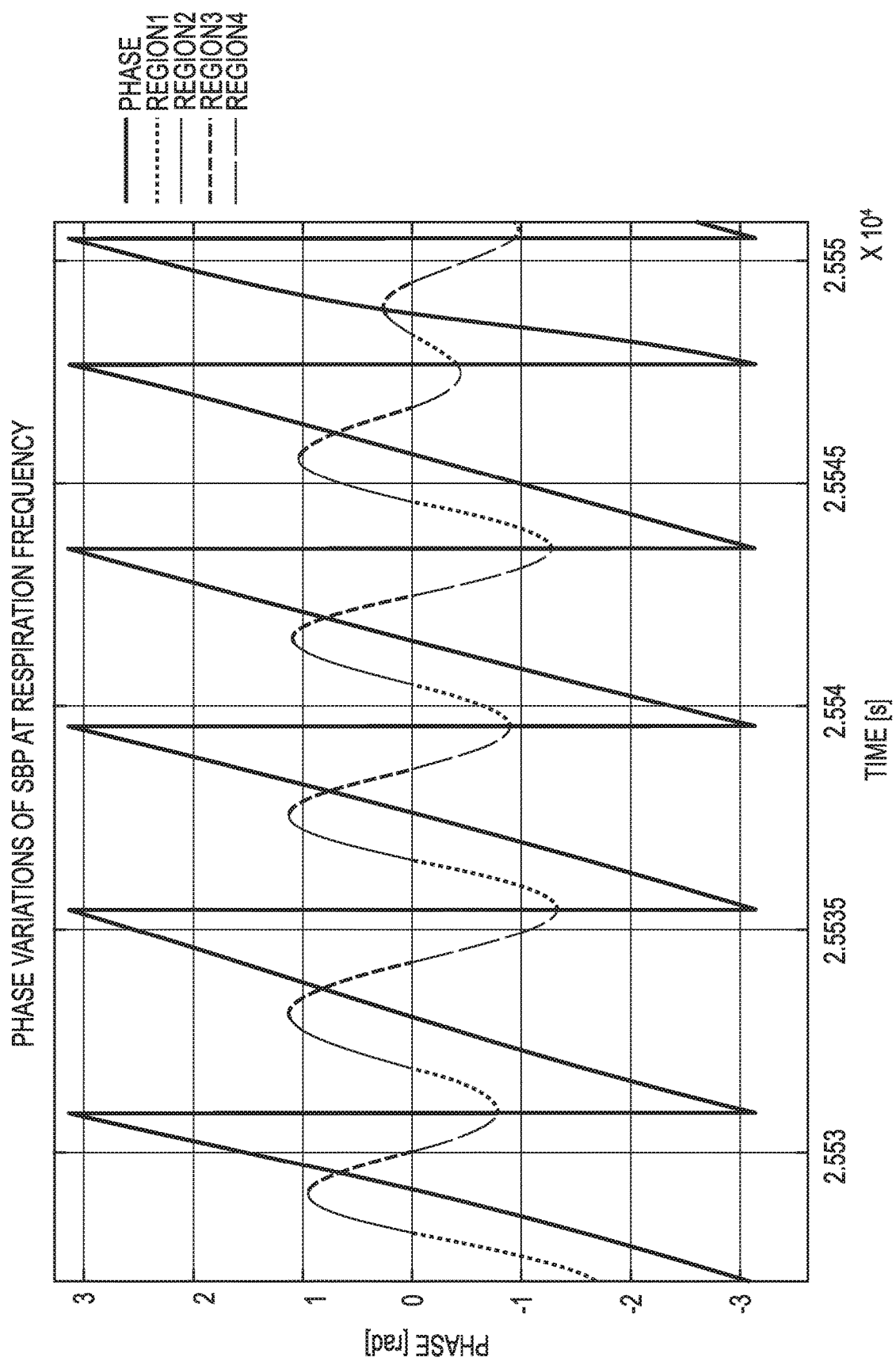

For example, FIG. 4A illustrates example peaks detected in a bio-signal indicative of BP. The peaks can include systolic, mean, and diastolic peaks compared to the continuous BP signal and as a function of time. Based on the peaks, one or more dominant frequencies of interest are identified, as shown by the frequencies of 0.06 Hz and 0.22 Hz in FIG. 4B. The BP signal is decomposed in the (or in each) dominant frequency of interest. For example, FIG. 4C illustrates the BP signal decomposed in the frequency of 0.06 Hz and FIG. 4D illustrates the BP signal decomposed in the frequency of 0.22 Hz (e.g., respiration frequency). Optimal windows for stimulus are determined using the decomposed BP signal in the dominant frequencies of interest. FIG. 4E illustrates phase variations of systolic BP at the respiration frequency of 0.22 Hz and as function of time. More specifically, FIG. 4E illustrates feature extraction for determining optimal windows (e.g., timings) for providing peripheral stimulation.

Table 1 below illustrates an example of properties of dominant PNS oscillations, in accordance with various embodiments:

| | | Stage: | | | | | | | | | | | | |
|---|---|---|---|---|---|---|---|---|---|---|---|---|---|---|
| | | N2 | | | N2 | | | | N3 | | | N3 | | |
| | | | | | Time: | | | | | | | | | |
| | | T1 | | | Tn | | | | T1 | | | Tn | | |
| | | #1 | #2 | #3 | ... #1 | #2 | #3 | ... #1 | #2 | #3 | ... #1 | #2 | #3 | ... |
| Heart rate | — | 0.04 Hz | 0.10 Hz | 0.20 Hz | ... — | 0.09 Hz | 0.21 Hz | ... — | 0.09 Hz | 0.19 Hz | ... | | | |
| Breathing | — | — | 0.20 Hz | — | ... — | — | 0.21 Hz | ... — | — | 0.20 Hz | ... | | | |
| Blood pressure | Systolic peak | — | 0.09 Hz | 0.20 Hz | ... | ... | ... | ... | ... | ... | ... | | | |
| | Diastolic peak | — | 0.09 Hz | 0.20 Hz | ... | ... | ... | ... | ... | ... | ... | | | |
| | Pulse pressure | 0.04 Hz | — | 0.20 Hz | ... | ... | ... | ... | ... | ... | ... | | | |
| PPG | Systolic peak | 0.04 Hz | 0.06 Hz | 0.20 Hz | ... | ... | ... | ... | ... | ... | ... | | | |
| ICG | Stroke volume | — | — | — | ... | ... | ... | ... | ... | ... | ... | | | |

-continued

| | Stage: | | | | | | | | | | | | | | | |
|---|---|---|---|---|---|---|---|---|---|---|---|---|---|---|---|---|
| | N2 | | | | N2 | | | | N3 | | | | N3 | | | |
| | | | | | Time: | | | | | | | | | | | |
| | T1 | | | | Tn | | | | T1 | | | | Tn | | | |
| | #1 | #2 | #3 | ... | #1 | #2 | #3 | ... | #1 | #2 | #3 | ... | #1 | #2 | #3 | ... |
| Pre-ejection period | 0.03 Hz | 0.15 Hz | — | ... | ... | ... | ... | ... | ... | ... | ... | ... | ... | ... | ... | ... |
| ... | ... | ... | ... | ... | ... | ... | ... | ... | ... | ... | ... | ... | ... | ... | ... | ... |

Properties of dominant PNS oscillation include, but are not limited to, features of dominant rhythms (e.g., amplitude, frequency, phase) across one or more bio-signals, redundancy among rhythms (e.g., the breathing frequency can be reflected on several CV measures) and phase shift among rhythms cam be calculated. Table 1 illustrates an example of extracted different dominant frequencies for different bio-signals, although embodiments are not so limited. More specifically, Table 1 illustrates examples of the dominant frequencies for several bio-signals in different sleep stages (e.g., N2 and N3) and for different times across the night. A dominant rhythm can be reflected in several bio-signals (e.g., breathing) and can vary across the night and for different sleep stages.

Figure 5:
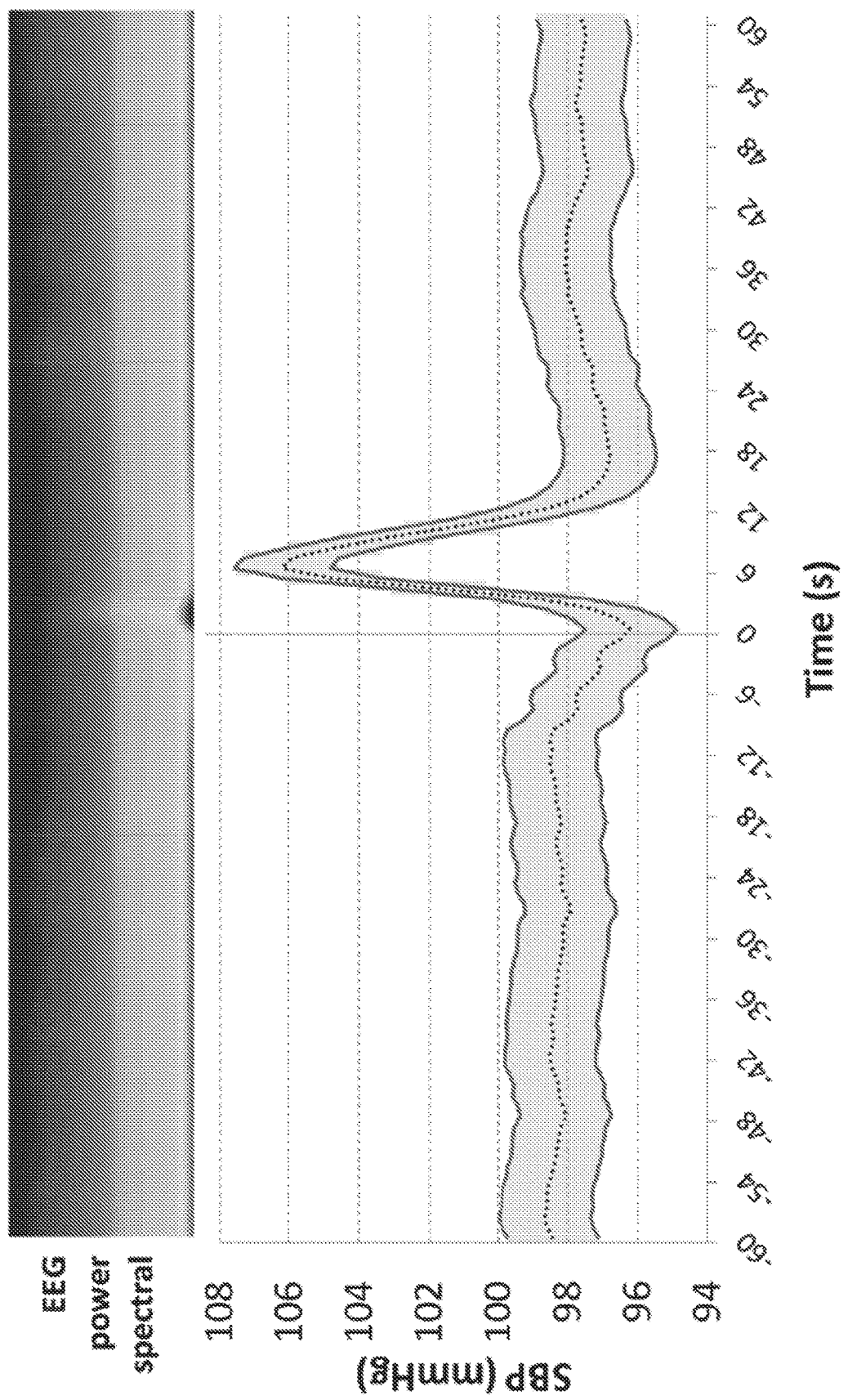
FIG. 5 illustrates example optimal windows for stimulation, in accordance with various embodiments.

FIG. 5 illustrates example optimal windows, in accordance with various embodiments. The theoretical rationale is based on the existence of multiple levels of coupling between brain and body signals. In particular, there can be specific time windows within dominant PNS oscillations (e.g., downward slope or phases of BP oscillations, phases of breathing), state (e.g., cardiac downregulation) and/or events (e.g., phasic cardiac oscillations) showing strong relationships with EEG features (e.g., increases in EEG SWA, isolated slow wave amplitude).

In addition, peripheral stimulation can elicit EEG SWA and autonomic oscillations with different features (e.g., different magnitudes and phase shifts) dependent on specific characteristics of the PNS oscillations (e.g., phases, timing within the cardiac cycle) at the time of stimulation, as well as depending on the type and characteristic of the stimulation (e.g., duration, intensity).

Figure 6A:
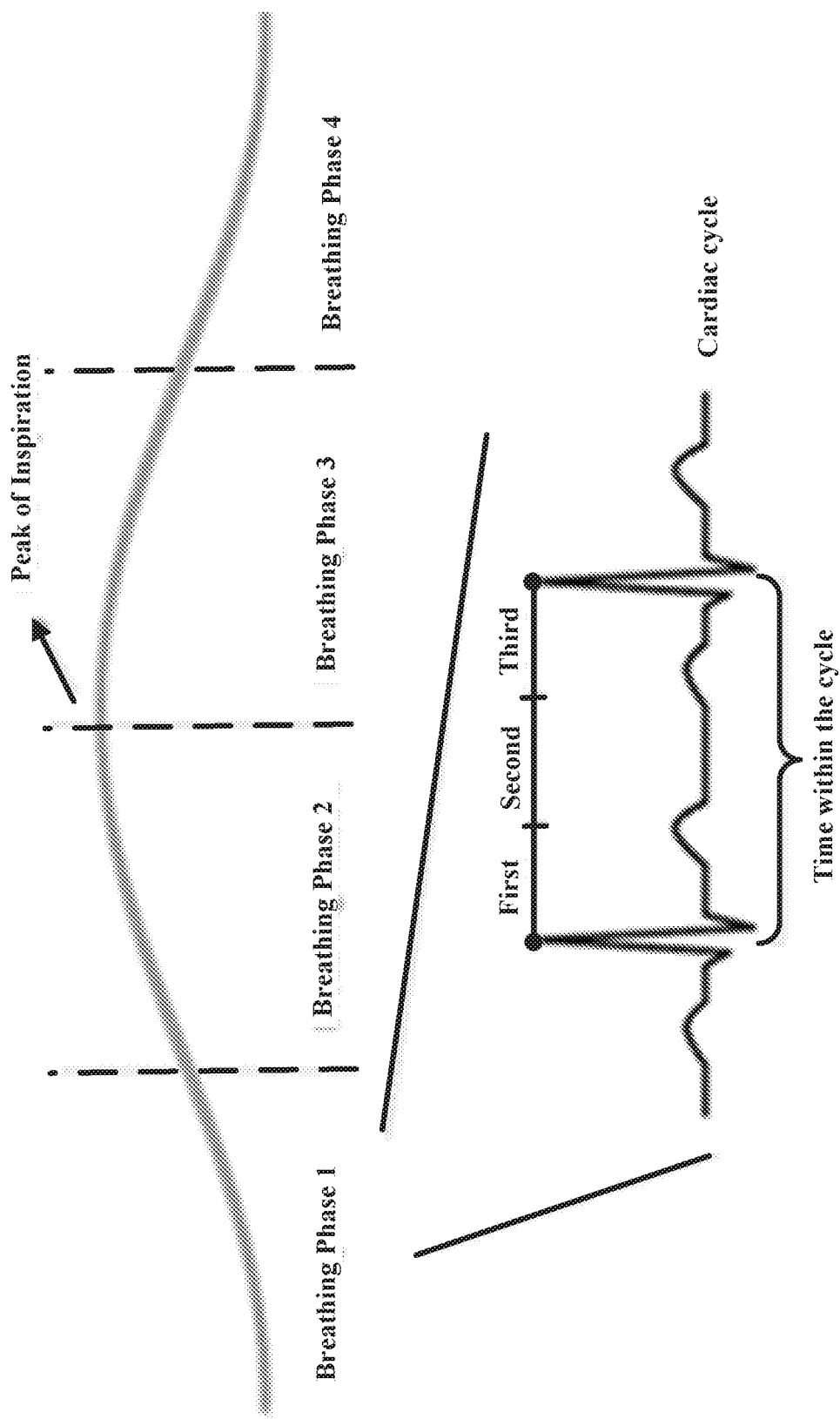
FIGS. 6A-6C illustrate example optimal windows for stimulation, in accordance with various embodiments.
Figure 6B:
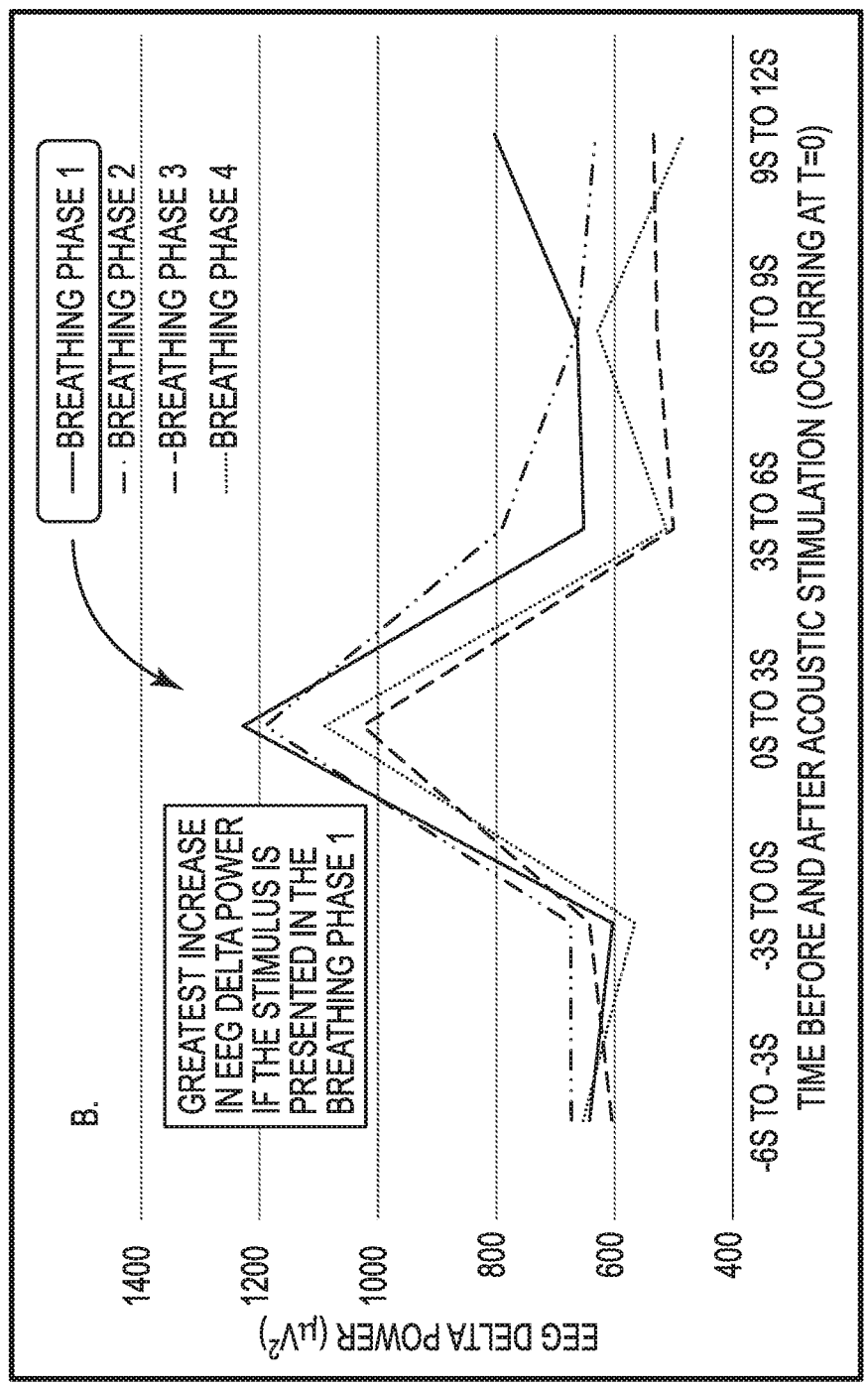
Figure 6C:
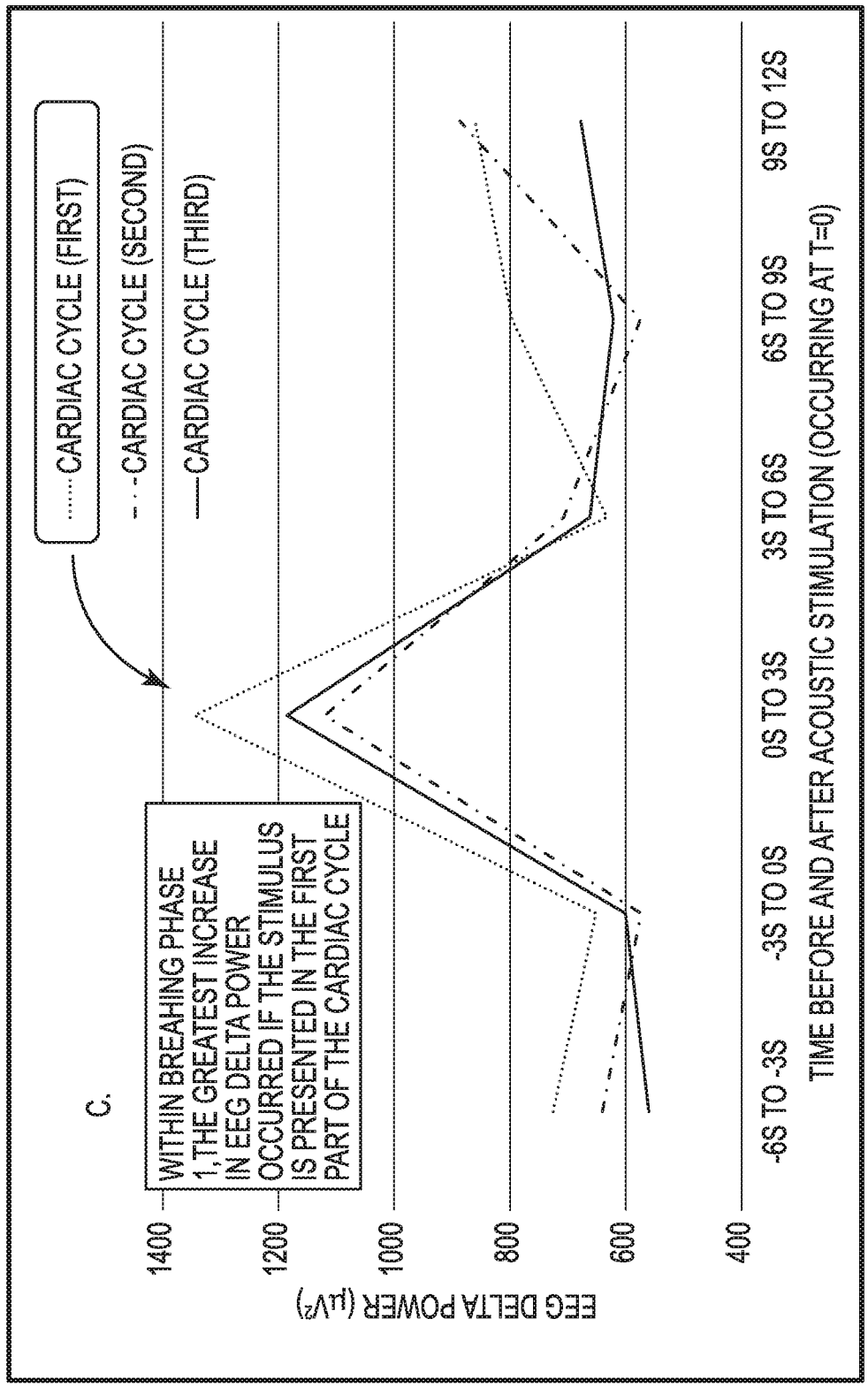

FIGS. 6A-6C illustrate example optimal windows for stimulation, in accordance with various embodiments. FIG. 6A illustrates, for example, optimal windows for peripheral rhythms of breathing and cardiac cycle. As shown, the breathing cycle can be separated into different phases, such as four breathing phases. In the specific embodiment, the breathing cycle is divided based on peaks in inspiration and expiration into four equal phases. However, embodiments are not so limited and the breathing cycle can be divided into eight phases or sixteen phases, among other variations. Similarly, the cardiac cycle is separated into different phases, such as the illustrated three cardiac phases, although embodiments are not so limited. The optimal window(s) includes a ROI of both the breathing and cardiac cycle during which stimulus-related enhancement of EEG SWA generation is maximized, although embodiments are not so limited and can be directed to and/or include other optimizations.

The bottom portion of FIG. 6A illustrates an example of cardiac phases in one cardiac cycle. The cardiac cycle can be divided into three phases or periods of equal length. The cardiac cycle, in this context, includes or refers to the time between subsequent ECG R-waves. The cardiac cycle can be also divided into more or fewer phases than illustrated, such as being divided based on more specific electrophysiological features (e.g., can be divided using p and t-waves in addition to the QRS complex).

FIG. 6B illustrates stimulation enhancement of SWA as compared to the breathing phases. In specific embodiments, acoustic stimulus of 1,000 Hz is provided to a user binaurally at 80 dB for 50 msec (e.g., 2 msec rise and fall time). Tone-related changes in EEG delta-power are displayed as function of time, before and after stimulation, and as a function of breathing phases in which the tones occur. In the specific embodiments, the greatest increase in EEG delta-power is evident in the 3 seconds following the stimulation, and the maximum peak EEG delta-power occurs when stimulus is provided in breathing phase one (see FIG. 6A). The lowest increase in EEG delta-power occurs when stimulus is provided in breathing phase three.

FIG. 6C illustrates tone-related change in EEG delta power within breathing phase one and as function of time, before and after stimulation, and as a function of cardiac phases in which the tones occur. As shown, the greatest increase in EEG delta-power occurs when the stimulation is delivered in the first phase of the cardiac cycle, compared to the second and third phases of cardiac cycle, for the specific embodiment. For this specific person, the greatest increase in EEG delta-power, which provides the optimal windows for stimulation, is evident for stimuli delivered within breathing phase one and in the first phase of cardiac cycle. In the specific example, the first phase of the breathing cycle correlates to time between the peak in expiration (e.g., minimum of the curve) and up to half-way between the peak in expiration and peak in inspiration.

Embodiments, which are not limited to the specific examples as illustrated above, are directed to enhancing SWA generation within a user based on dominant PNS oscillations and as a function of sleep stages and time of night. Apparatuses and methods of using the same involve providing closed-loop stimulation in which user response to stimulation is feedback to the system and used to further refine the timing of stimulation. Enhancing EEG SWA can be useful for a variety of purposes, such as the treatment of diseases and conditions.

Various embodiments are implemented in accordance with embodiments in U.S. Provisional Application (62/533, 299), entitled "Overclocking the Human System by Optimizing and Hacking the Brain-Body Interplay During EEG Slow Wave Deep state," filed Jul. 17, 2017, which is fully incorporated herein by reference. For instance, the embodiments described therein may be combined in varying degrees (including wholly) with the embodiments described above. As a specific example, which is described above in connection with FIGS. 1A-1B, EEG SWA optimization, as described by various embodiments herein can be implemented in accordance with stimulation applied as described and illustrated by FIG. 1 of U.S. Provisional Application 62/533,299. Embodiments discussed in the U.S. Provisional Application are not intended, in any way, to be limiting to the overall technical disclosure, or to any part of the claimed invention unless specifically noted.

The skilled artisan would recognize that various terminology as used in the Specification (including claims) connote a plain meaning in the art unless otherwise indicated. As examples, the Specification describes and/or illustrates aspects useful for implementing the claimed disclosure by way of various circuits or circuitry which may be illustrated as or using terms such as blocks, modules, device, system, unit, controller, and/or other circuit-type depictions (e.g., reference numerals 104, 106, 108 of FIG. 1A depict a block/module as described herein). Such circuits or circuitry are used together with other elements to exemplify how certain embodiments may be carried out in the form or structures, steps, functions, operations, activities, etc. For example, in certain of the above-discussed embodiments, one or more modules are discrete logic circuits or programmable logic circuits configured and arranged for implementing these operations/activities, as may be carried out in the approaches shown in FIG. 1B and FIG. 2. In certain embodiments, such a programmable circuit is one or more computer circuits, including memory circuitry for storing and accessing a program to be executed as a set (or sets) of instructions (and/or to be used as configuration data to define how the programmable circuit is to perform), and an algorithm or process as described at FIGS. 3A-3B is used by the programmable circuit to perform the related steps, functions, operations, activities, etc. Depending on the application, the instructions (and/or configuration data) can be configured for implementation in logic circuitry, with the instructions (whether characterized in the form of object code, firmware or software) stored in and accessible from a memory (circuit).

Various embodiments described above, and discussed provisional application may be implemented together and/or in other manners. One or more of the items depicted in the present disclosure and in the underlying provisional application can also be implemented separately or in a more integrated manner, or removed and/or rendered as inoperable in certain cases, as is useful in accordance with particular applications. In view of the description herein, those skilled in the art will recognize that many changes may be made thereto without departing from the spirit and scope of the present disclosure.

What is claimed is:

1. A method for enhancing slow wave activity (SWA), comprising:
   receiving a plurality of bio-signals from a user;
   classifying sleep stages using the plurality of bio-signals;
   determining a dominant oscillation in a peripheral nervous system (PNS) bio-signal of the plurality of bio-signals as a function of time and the sleep stages by:
      calculating a power spectral density (PSD) indicative of oscillations in the PNS bio-signal, and
      detecting a peak in the PSD as the dominant oscillation, wherein the dominant oscillation is a rhythm of the PNS bio-signal occurring at a dominant frequency, the dominant frequency including a frequency of the PSD at the peak, and wherein the PNS bio-signal is selected from the group consisting of:
      blood pressure, heart rate, breathing, a pulse wave, and a combination thereof;
   characterizing a property of the dominant oscillation including at least one of a phase, a phase shift, an amplitude, and a frequency of the dominant oscillation by:
      decomposing the PNS bio-signal in the dominant frequency as a function of time using a filter to filter out frequency content other than the dominant frequency and identifying the property from the decomposed PNS bio-signal;
   providing an indication of an optimal window, based on timing of the property as characterized from the decomposed PNS bio-signal for maximizing SWA generation, to stimulation circuitry configured and arranged to deliver stimulation to the user within the optimal window, wherein the optimal window is selected based on data indicating stimulation improves electroencephalogram (EEG) SWA within the user during the optimal window, the data comprising past observed responses to prior stimulation including measures of EEG and the PNS bio-signal; and
   providing feedback responsive to the stimulation based on an EEG signal of the user.

2. The method of claim 1, wherein characterizing the property of the dominant oscillation in the PNS bio-signal includes characterizing dominant rhythms across the PNS bio-signal, redundancy among rhythms of different bio-signals of the plurality of bio-signals, and phase shifts, and wherein the plurality of bio-signals includes at least two different types of bio-signals including the PNS bio-signal.

3. The method of claim 1, further including adapting and optimizing timing of the stimulation according to the phase of the dominant oscillation based on the feedback and to maximize SWA for the user, wherein the feedback includes user response to the stimulation including the measure of EEG delta power as a function of the stimulation and the PNS bio-signal, wherein the optimal window is determined based on properties of two or more dominant oscillations associated with two or more PNS bio-signals, wherein the two or more dominant oscillations are selected from the group consisting of: the dominant oscillation and are PNS bio-signals selected from heart rate, blood pressure, and a combination thereof.

4. The method of claim 1, further including providing pre-stimulation of the PNS by providing peripheral neuro-modulations according to the phase of the dominant oscillation to optimize a state of the PNS prior to providing the stimulation for maximizing SWA enhancement by the stimulation circuitry, wherein the PNS bio-signal is selected from the group consisting of:
   beat-to-beat blood pressure, heart rate, pre-ejection period (PEP) from impedance cardiography (ICG), and a combination thereof, and
   the property is frequency or phase.

5. The method of claim 1, wherein classifying sleep stages further includes processing the plurality of bio-signals in combination with photoplethysmographic (PPG)-derived HR variability (HRV) measures or using motion in combination with EEG and electrooculographic (EOG) signals, and the plurality of bio-signals include beat-to-beat blood pressure, heart rate, and pre-ejection period (PEP) from impedance cardiography (ICG); and
   wherein the data indicating stimulation improves EEG SWA is selected from the group consisting of:
      data used to train a machine learning module;
      observed responses of the user to the prior stimulation; and
      a combination thereof.

6. The method of claim 1, wherein the optimal window is for at least one of an autonomic nervous system (ANS) bio-signal, cardiovascular (CV) rhythm, and other bio-signals, and wherein:
the PNS bio-signal comprises blood pressure and the property of the dominant oscillation comprises frequency or phase; and
providing the optimal window includes segmenting the decomposed PNS bio-signal into several windows, and selecting the optimal window from the several windows based on the data indicating stimulation improves EEG SWA within the user, wherein the dominant oscillation shows a relations with EEG features in the optimal window.

7. The method of claim 1, wherein the phase of the dominant frequency associated with the dominant oscillation is used to determine the optimal window for delivering stimulation to the user for maximizing EEG SWA within the user and the PNS bio-signal comprises blood pressure, and wherein the peak is associated with the dominant frequency of the PNS bio-signal.

8. A non-transitory computer-readable storage medium having stored thereon program instructions executable by processing circuitry to perform the method of claim 1.

9. An apparatus for enhancing slow wave activity (SWA), comprising:
data transmission circuitry configured and arranged to receive a plurality of bio-signals as obtained from a user by sensor circuitry having one or more bio-sensors, the plurality of bio-signals including peripheral nervous system (PNS) bio-signals and central nervous system (CNS) bio-signals;
processing circuitry configured and arranged to:
classify a plurality of sleep stages using a PNS bio-signal of the PNS bio-signals;
calculating a power spectral density (PSD) indicative of oscillations in the PNS bio-signal and detecting a peak in the PSD as a dominant oscillation in the PNS bio-signal, wherein the dominant oscillation is a rhythm of the PNS bio-signal occurring at a dominant frequency, and the dominant frequency including a frequency of the PSD at the peak and wherein the PNS bio-signal is selected from the group consisting of: blood pressure, heart rate, breathing, a pulse wave, and a combination thereof;
characterize properties of the dominant oscillation including a phase, an amplitude, and a frequency of the dominant oscillation by:
decomposing the PNS bio-signal in the dominant frequency as a function of time using a filter to filter out frequency content other than the dominant frequency and identifying the properties from the decomposed PNS bio-signal; and
determine optimal windows based on timings of the phase of the dominant frequency as characterized from the decomposed PNS bio-signal, wherein the optimal windows are selected based on data indicating a stimulation or a series of stimulations improves electroencephalogram (EEG) SWA within the user during the optimal windows, the data comprising past observed responses to prior stimulation including measures of EEG and the PNS signals,
wherein the data transmission circuitry is further configured and arranged to output an indication of the determined optimal windows to stimulation circuitry configured and arranged to deliver stimulation to the user within the optimal window of the determined optimal windows for maximizing EEG SWA generation.

10. The apparatus of claim 9, further including feedback circuitry configured and arranged to provide a feedback signal indicative of a user response to the stimulation based on an EEG signal obtained from the user, wherein the user response includes the measure of EEG delta power as a function of the stimulation and at least a portion of the plurality of bio-signals.

11. The apparatus of claim 10, wherein the processing circuitry is further configured and arranged with the feedback circuitry to improve CV function or other features of the PNS bio-signals and CNS bio-signals based on the feedback signal by adjusting the optimal window based on the EEG delta power.

12. The apparatus of claim 9, wherein the processing circuitry includes:
data processing circuitry configured and arranged to determine the optimal windows; and
feedback circuitry configured and arranged to provide a feedback signal indicative of a user response to the stimulation based on an EEG signal of the user,
wherein the data processing circuitry is further configured and arranged to adjust the optimal windows based on the feedback signal to optimize EEG SWA, the feedback signal including the EEG signal as obtained by the sensor circuitry while the stimulation circuitry delivers the stimulation to the user within the optimal window of the determined optimal windows.

13. The apparatus of claim 9, further including the stimulation circuitry which is configured and arranged to provide at least one of an acoustic stimulation, a haptic stimulation, electrical stimulation haptic and neuromodulation, wherein the data indicating stimulation improves EEG SWA includes observed responses of other users to the prior stimulation.

14. The apparatus of claim 9, further including the sensor circuitry having at least two bio-sensors and configured and arranged to obtain at least two different types of PNS bio-signals, the at least two different types of PNS bio-signals including the PNS bio-signal, and the processing circuitry is configured and arranged to determine the optimal windows responsive to the phase of dominant oscillations associated with the two different types of PNS bio-signals, the dominant oscillations including the dominant oscillation in the PNS bio-signal, and wherein the two different types of PNS bio-signals are blood pressure and heart rate.

15. The apparatus of claim 9, wherein the processing circuitry is configured and arranged to classify sleep stages by at least one of:
extracting EEG features from an EEG signal; and
extracting other physiological features from the one or more bio-sensors.

16. The apparatus of claim 9, wherein the processing circuitry is configured and arranged to optimize EEG SWA generation by quantifying spectral analysis of an EEG signal within a frequency of interest.

17. An apparatus including:
sensor circuitry having at least two bio-sensors configured and arranged to obtain a plurality of bio-signals, which include peripheral nervous system (PNS) bio-signals and signals indicative of sleep stages, from a user and to provide output signals indicative of the plurality of bio-signals to processing circuitry, wherein each of the PNS bio-signals are selected from the group consisting of: blood pressure, heart rate, breathing, a pulse wave, and a combination thereof;

the processing circuitry configured and arranged to:
classify a plurality of sleep stages using the signals indicative of the sleep stages using the plurality of bio-signals;
calculate a power spectral density (PSD) for each of the PNS bio-signals, the PSD for each of the PNS bio-signals being indicative of oscillations in the PNS bio-signals;
determine peaks in the PSD for each of the PNS bio-signals;
determine dominant oscillations associated with each of the PNS bio-signals based on the peaks in the PSD for each of the PNS bio-signals as a function of the sleep stages and time, wherein each of the dominant oscillations is a rhythm of the respective PNS bio-signal that occurs at a respective dominant frequency, and the respective dominant frequency includes a frequency of the PSD at the respective peak;
characterize properties of the dominant oscillations including an amplitude, phase, and frequency of the dominant oscillations by:
decomposing each of the PNS bio-signals in the respective dominant frequency as functions of time using filters to filter out frequency content other than the respective dominant frequency for each of the PNS bio-signals and identifying the properties from the decomposed PNS bio-signals; and
determine optimal windows based on timings of the properties as characterized from the decomposed PNS bio-signals, the properties including at least the phase of the dominant oscillations, for maximizing SWA generation via stimulation, wherein the optimal windows are determined based on data indicating stimulation provided to the user improves electroencephalogram (EEG) SWA within the user during the optimal windows, the data comprising past observed responses to prior stimulation including measures of EEG and the PNS signals;

stimulation circuitry configured and arranged to deliver the stimulation to the user within an optimal window of the optimal windows for maximizing EEG SWA generation; and
feedback circuitry configured and arranged to provide a feedback signal to the processing circuitry, the feedback signal being indicative of a user response to the stimulation based on an EEG signal of the user and the processing circuitry is further configured and arranged to adjust the optimized windows based on the user response to the stimulation and as indicated in the feedback signal.

18. The apparatus of claim 17, wherein the sensor circuitry includes an EEG sensor configured and arranged to provide the EEG signal to the feedback circuitry in response to the stimulation circuitry delivering the stimulation to the user, and wherein the data indicating stimulation improves EEG SWA includes observed responses of the user to the prior stimulation.

19. The apparatus of claim 17, wherein the sensor circuitry includes a blood pressure (BP) sensor configured and arranged to provide a bio-signal indicative of BP among the plurality of bio-signals and the processing circuitry is configured and arranged to:
determine the dominant oscillations as the function of the sleep stages and time by:
detecting the peaks in BP using the PSD of the bio-signal indicative of BP;
determining the respective dominant frequency associated with BP based on the detected peaks in the PSD of the bio-signal indicative of BP;
decomposing the bio-signal indicative of BP in the dominant frequency using a respective filter of the filters; and
determining the optimal windows for stimulation based on the decomposed bio-signal indicative of BP in the dominant frequency.

20. The apparatus of claim 17, wherein the processing circuitry is configured and arranged to determine the dominant oscillations based on the dominant frequencies associated with the peaks of the PNS bio-signals and during N2 and N3 stages of sleep.

* * * * *